(12) United States Patent
Weiman et al.

(10) Patent No.: US 12,295,862 B2
(45) Date of Patent: *May 13, 2025

(54) EXPANDABLE FUSIONS DEVICES, INSTRUMENTS, AND METHODS THEREOF

(71) Applicant: GLOBUS MEDICAL, INC., Audubon, PA (US)

(72) Inventors: Mark Weiman, Downingtown, PA (US); Hilliary Kopp, Virginia Beach, VA (US); Joel Cryder, Warrington, PA (US); James Himmelberger, Souderton, PA (US); Jason Gray, East Greenville, PA (US); Jason Zappacosta, Philadelphia, PA (US); Mark Miccio, Lynbrook, NY (US); Shawn Cox, Reading, PA (US); David Feigenbaum, Philadelphia, PA (US); Damien Kahmer, Warrington, PA (US)

(73) Assignee: Globus Medical Inc., Audubon, PA (US)

(*) Notice: Subject to any disclaimer, the term of this patent is extended or adjusted under 35 U.S.C. 154(b) by 85 days.

This patent is subject to a terminal disclaimer.

(21) Appl. No.: 18/325,633

(22) Filed: May 30, 2023

(65) Prior Publication Data
US 2023/0301797 A1 Sep. 28, 2023

Related U.S. Application Data

(63) Continuation of application No. 17/506,754, filed on Oct. 21, 2021, now Pat. No. 11,737,891, which is a (Continued)

(51) Int. Cl.
A61F 2/44 (2006.01)
A61F 2/46 (2006.01)
A61F 2/30 (2006.01)

(52) U.S. Cl.
CPC .............. *A61F 2/447* (2013.01); *A61F 2/442* (2013.01); *A61F 2/4611* (2013.01); *A61F 2002/30131* (2013.01); *A61F 2002/30579* (2013.01)

(58) Field of Classification Search
CPC .......... A61F 2/44; A61F 2/442; A61F 2/4455; A61F 2/446; A61F 2/4465; A61F 2/447;
(Continued)

(56) References Cited

U.S. PATENT DOCUMENTS

| | | |
|---|---|---|
| 4,349,921 A | 9/1982 | Kuntz |
| 4,599,086 A | 7/1986 | Doty |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Eric S Gibson

(57) ABSTRACT

Expandable fusion devices, systems, instruments, and methods thereof. The expandable fusion device is capable of being installed inside an intervertebral disc space to maintain normal disc spacing and restore spinal stability, thereby facilitating an intervertebral fusion. The fusion device may include a body, a first endplate, and a second endplate. A drive screw may be rotated to move the first and second endplates outwardly and into an expanded configuration. Instruments may be provided to ensure the implant is inserted safely and as intended.

18 Claims, 26 Drawing Sheets

Related U.S. Application Data continuation of application No. 16/779,756, filed on Feb. 3, 2020, now Pat. No. 11,191,650.

(58) Field of Classification Search
CPC .......... A61F 2/4611; A61F 2002/30266; A61F 2002/30398; A61F 2002/30476; A61F 2002/30495; A61F 2002/30507; A61F 2002/30514; A61F 2002/30537; A61F 2002/30538; A61F 2002/30556; A61F 2002/30579; A61F 2002/30593; A61F 2002/4627; A61F 2002/4629
See application file for complete search history.

(56) References Cited

U.S. PATENT DOCUMENTS

| | | |
|---|---|---|
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A * | 9/1996 | Lahille ............... A61F 2/447 |
| | | 606/247 |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 * | 3/2012 | Kostuik ............... A61F 2/447 |
| | | 606/287 |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | Jimenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | Jimenez et al. |
| 9,532,883 B2 | 1/2017 | McLuen et al. |
| 9,622,878 B2 | 4/2017 | Grotz |
| 10,022,239 B1 | 7/2018 | Lentner et al. |
| 10,709,573 B2 * | 7/2020 | Weiman ............... A61F 2/442 |
| 10,758,367 B2 * | 9/2020 | Weiman ............... A61F 2/442 |
| 10,869,768 B2 * | 12/2020 | Weiman ............... A61F 2/447 |
| 10,973,657 B2 * | 4/2021 | Remington ........... A61F 2/447 |
| 11,191,650 B2 * | 12/2021 | Weiman ............... A61F 2/4455 |
| 11,737,891 B2 * | 8/2023 | Weiman ............... A61F 2/4455 |
| | | 623/17.16 |
| 2002/0045945 A1 | 4/2002 | Liu |
| 2002/0068976 A1 * | 6/2002 | Jackson ............... A61F 2/447 |
| | | 623/17.15 |
| 2002/0068977 A1 * | 6/2002 | Jackson ............... A61F 2/4455 |
| | | 606/247 |
| 2004/0030387 A1 | 2/2004 | Landry |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 * | 2/2005 | Gordon ............... A61F 2/4425 |
| | | 606/247 |
| 2005/0080422 A1 | 4/2005 | Otte |
| 2005/0113916 A1 | 5/2005 | Branch |
| 2005/0149188 A1 | 7/2005 | Cook |
| 2005/0171541 A1 * | 8/2005 | Boehm ............... A61F 2/446 |
| | | 606/247 |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish et al. |
| 2006/0015184 A1 | 1/2006 | Winterbottom |
| 2006/0058878 A1 | 3/2006 | Michelson |
| 2006/0084986 A1 | 4/2006 | Grinberg |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 * | 8/2006 | Gordon ............... A61B 17/7052 |
| | | 606/247 |
| 2006/0229729 A1 * | 10/2006 | Gordon ............... A61F 2/4425 |
| | | 623/17.16 |
| 2006/0241770 A1 | 10/2006 | Rhoda |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |

(56) References Cited

U.S. PATENT DOCUMENTS

| | | |
|---|---|---|
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1* | 1/2008 | Thramann ............... A61F 2/447 623/17.16 |
| 2008/0065222 A1 | 3/2008 | Hamada |
| 2008/0114467 A1 | 5/2008 | Capote |
| 2008/0140207 A1* | 6/2008 | Olmos .................. A61F 2/4455 623/17.11 |
| 2008/0147194 A1 | 6/2008 | Grotz |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0076616 A1 | 3/2009 | Duggal |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger |
| 2010/0286783 A1 | 11/2010 | Lechmann |
| 2011/0035011 A1 | 2/2011 | Cain |
| 2011/0093074 A1 | 4/2011 | Glerum |
| 2011/0160861 A1 | 6/2011 | Jimenez |
| 2011/0172774 A1 | 7/2011 | Varela |
| 2011/0276142 A1 | 11/2011 | Niemiec |
| 2011/0301713 A1 | 12/2011 | Theofilos |
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0109308 A1 | 5/2012 | Lechmann |
| 2012/0130496 A1 | 5/2012 | Duffield |
| 2012/0165945 A1 | 6/2012 | Hansell |
| 2012/0185049 A1* | 7/2012 | Varela .................... A61F 2/447 623/17.16 |
| 2012/0209386 A1 | 8/2012 | Triplett |
| 2012/0215313 A1 | 8/2012 | Saidha |
| 2012/0265309 A1* | 10/2012 | Glerum .................. A61F 2/447 623/17.16 |
| 2012/0277861 A1 | 11/2012 | Steele et al. |
| 2012/0277870 A1 | 11/2012 | Wolters |
| 2012/0323329 A1 | 12/2012 | Jimenez |
| 2012/0330426 A1 | 12/2012 | Mclaughlin |
| 2013/0023993 A1* | 1/2013 | Weiman ................. A61F 2/4611 623/17.16 |
| 2013/0023994 A1* | 1/2013 | Glerum .................. A61F 2/447 623/17.16 |
| 2013/0158669 A1* | 6/2013 | Sungarian ............... A61F 2/442 623/17.16 |
| 2013/0274883 A1 | 10/2013 | McLuen et al. |
| 2014/0067071 A1* | 3/2014 | Weiman ................. A61F 2/4611 623/17.16 |
| 2014/0088714 A1 | 3/2014 | Miller et al. |
| 2014/0236296 A1* | 8/2014 | Wagner ................. A61F 2/4611 623/17.15 |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1* | 12/2015 | Sandul .................. A61F 2/4455 623/17.16 |
| 2016/0151168 A1* | 6/2016 | Weiman .................... A61F 2/44 623/17.16 |
| 2016/0166396 A1* | 6/2016 | McClintock ............ A61F 2/446 623/17.16 |
| 2016/0256291 A1* | 9/2016 | Miller ................... A61F 2/4611 |
| 2016/0324654 A1 | 11/2016 | Loebl et al. |
| 2016/0354211 A1* | 12/2016 | Packer ................... A61F 2/4611 |
| 2016/0361176 A1* | 12/2016 | Weiman .................... A61F 2/44 |
| 2017/0100258 A1 | 4/2017 | Jimenez et al. |
| 2017/0119543 A1 | 5/2017 | Dietzel et al. |
| 2017/0304066 A1* | 10/2017 | Smith .................. A61B 17/025 |
| 2018/0049890 A1* | 2/2018 | Popejoy ............... A61B 17/8833 |
| 2018/0177603 A1* | 6/2018 | Weiman ................. A61F 2/442 |
| 2018/0177604 A1* | 6/2018 | Weiman ................. A61F 2/4611 |
| 2018/0185163 A1* | 7/2018 | Weiman ................. A61F 2/442 |
| 2018/0200078 A1* | 7/2018 | Remington ........... A61F 2/4611 |
| 2019/0083283 A1* | 3/2019 | Sharifi-Mehr ........ A61F 2/4611 |
| 2020/0315811 A1* | 10/2020 | Cryder ................. A61F 2/442 |
| 2021/0128319 A1* | 5/2021 | Tseng ................. A61B 17/8858 |
| 2021/0186706 A1* | 6/2021 | Spitler ..................... A61F 2/44 |
| 2021/0236298 A1* | 8/2021 | Weiman ................. A61F 2/442 |
| 2021/0275318 A1* | 9/2021 | Reimels ................ A61F 2/4455 |
| 2021/0275319 A1* | 9/2021 | Reimels ................ A61F 2/4611 |
| 2022/0039964 A1* | 2/2022 | Weiman ................. A61F 2/442 |
| 2023/0301797 A1* | 9/2023 | Weiman ................. A61F 2/442 |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| EP | 3479799 A1 | 5/2019 |
| FR | 2794968 | 12/2000 |
| JP | 2000-513263 | 10/2000 |
| JP | 2014531921 A | 12/2014 |
| JP | 2019500165 A | 1/2019 |
| JP | 2019084358 A | 6/2019 |
| SU | 1424826 A1 | 9/1988 |
| WO | 9201428 A1 | 2/1992 |
| WO | 9525485 A1 | 9/1995 |
| WO | 199942062 A1 | 8/1999 |
| WO | 199966867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2012031267 A1 | 3/2012 |
| WO | 2017117513 A1 | 7/2017 |

* cited by examiner

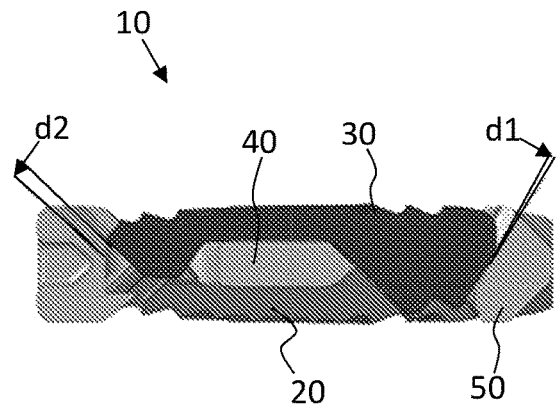
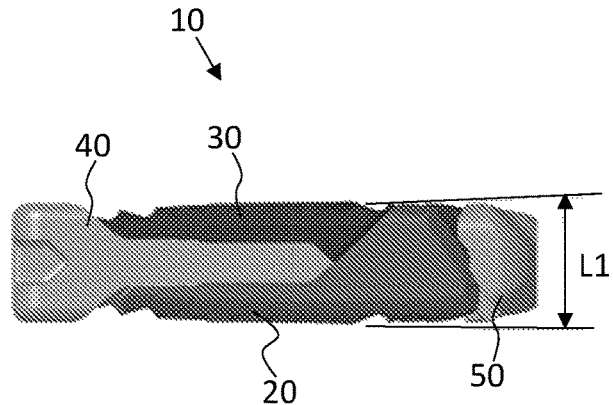
FIG. 6
FIG. 7
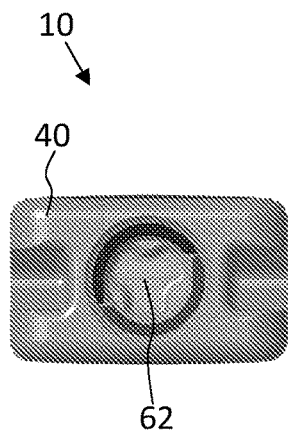
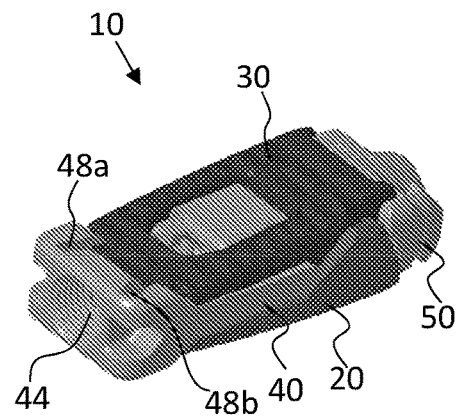
FIG. 8
FIG. 9

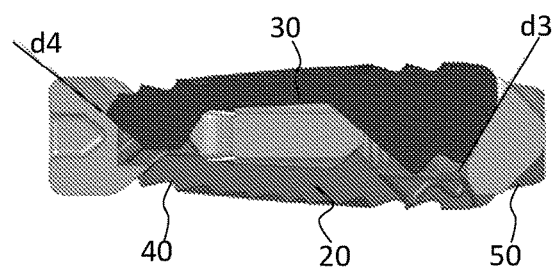
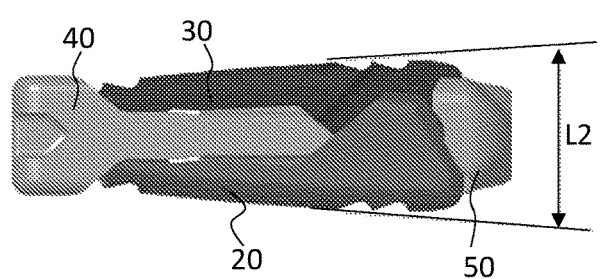
FIG. 10  FIG. 11
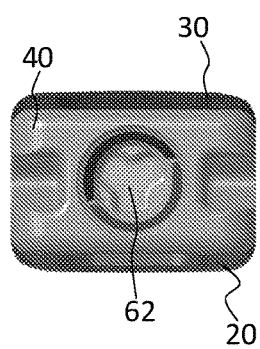
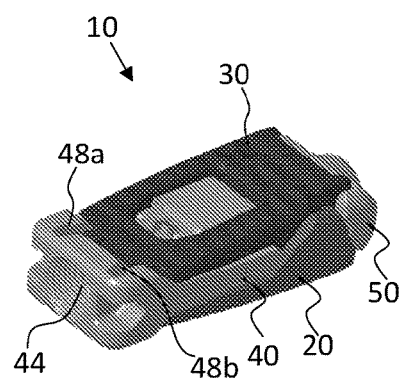
FIG. 12  FIG. 13

EXPANDABLE FUSIONS DEVICES, INSTRUMENTS, AND METHODS THEREOF

CROSS-REFERENCE TO RELATED APPLICATIONS

This patent application is a continuation of U.S. patent application Ser. No. 17/506,754, filed Oct. 21, 2021 (published as U.S. Pat. Pub. No. 2022-0039964), which is a continuation of U.S. patent application Ser. No. 16/779,756, filed on Feb. 3, 2020, now U.S. Pat. No. 11,191,650, all of which are incorporated in their entireties herein for all purposes.

FIELD OF THE INVENTION

The present disclosure relates to surgical devices, and more particularly, to expandable fusion devices capable of being installed inside an intervertebral disc space and then expanded to maintain disc spacing, restore spinal stability, and facilitate an intervertebral fusion. The present disclosure further relates to instruments for installing the same.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for a fusion device capable of being installed inside an intervertebral disc space at a minimum to no distraction height and for a fusion device that can maintain a normal distance between adjacent vertebral bodies when implanted.

SUMMARY OF THE INVENTION

In accordance with the application, devices, systems, methods, and instruments are provided. In particular, an expandable fusion device is provided, which is capable of being installed inside an intervertebral disc space to maintain normal disc spacing and restore spinal stability, thereby facilitating an intervertebral fusion. The device may be installed in an open, semi-open, or minimally invasive surgical procedure. The expandable fusion device may be capable of being placed into the disc space down an endoscopic tube, for example, and then expanded into the expanded configuration.

According to one embodiment, an implantable system includes an expandable device having a first endplate and a second endplate, a body positioned between the first endplate and the second endplate, and a drive screw and a lock positioned within the body. Rotation of the drive screw is configured to increase or decrease a distance between the first endplate and the second endplate, and the lock is configured to stop rotation of the drive screw. The drive screw may have a head portion and a shaft. The head portion may have a plurality of protrusions defining a plurality of notches therebetween, an annular ring, and a circumferential groove between the plurality of protrusions and the annular ring. The lock may have a first ring and a second ring connected to the first ring by a strut. In a locked position, the second ring may be configured to rest in the circumferential groove of the head portion, the strut may be located in one of the notches, and the first ring of the lock may rest on a top face of the head portion of the drive screw. In an unlocked position, the second ring may be translated out of the groove, and the strut may be translated out of the notch in order to permit the drive screw to be rotated by a driver instrument.

According to one embodiment, an inserter instrument includes an inserter sleeve, a threaded shaft, and a driver. The inserter sleeve may include an inserter body with a guide shaft extending from a proximal end to a distal end, and a handle at the proximal end. The guide shaft may include a tubular member defining a channel therethrough. A first plurality of splines may be defined within the channel at the proximal end. The threaded shaft may be positionable through the channel of the inserter sleeve. The threaded shaft may include a cannulated connector shaft and a slide including a second plurality of splines configured to engage with the first plurality of splines. The driver may be positionable through the threaded shaft. The driver may include a shaft with a linear cam configured to engage the slider of the threaded shaft. When the driver is positioned through the threaded shaft and the linear cam engages the slider, the slider linearly translates towards the distal end, thereby causing the first and second plurality of splines to mate, and thereby locking an implant to the inserter instrument.

According to another embodiment, a system for installing an expandable implant includes the expandable implant and an inserter instrument. The expandable implant may include a first endplate, a second endplate, a body positioned between the first endplate and the second endplate, and a drive screw positioned within the body. Rotation of the drive screw may be configured to increase or decrease a distance between the first endplate and the second endplate. The inserter instrument may include an inserter sleeve, a threaded shaft positionable through the inserter sleeve, and a driver positionable through the threaded shaft. The inserter sleeve may include a guide shaft defining a channel therethrough, and a first plurality of splines defined within the channel. The threaded shaft may include a slide having a second plurality of splines configured to engage with the first plurality of splines. The driver may include a linear cam configured to engage the slider of the threaded shaft. When the driver is positioned through the threaded shaft and the linear cam engages the slider, the slider linearly translates forward, thereby causing the first and second plurality of splines to mate, and thereby locking the implant to the inserter instrument.

According to another embodiment, methods of installing the expandable implant are provided. A disc space of a patient may be accessed and prepared. Opposed tabs at the distal end of the inserter sleeve may engage corresponding recesses on the implant. The threaded shaft may be positioned through the inserter sleeve and a threaded distal tip of the threaded shaft may threadedly engage the implant. The implant may be positioned within the disc space. A driver may be positioned through the threaded shaft. The linear cam of the driver may slide forward the slider of the threaded shaft causing the first and second plurality of splines to mate and locking the implant to the inserter instrument. The driver tip engages a corresponding recess in the head of the drive screw of the implant. The driver rotates the drive screw of the implant, thereby expanding the implant to the proper disc height. The implant may not be released until the driver is withdrawn from the threaded shaft, thereby disengaging the splines.

Also provided are kits including expandable fusion devices of varying types and sizes, rods, fasteners or anchors, k-wires, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 6 shows a cross-sectional view of the expandable fusion device at the contracted height;

FIG. 7 shows a side view of the expandable fusion device at the contracted height;

FIG. 8 shows a back view of the expandable fusion device at the contracted height;

FIG. 9 shows a perspective view of the expandable fusion device at the contracted height;

FIG. 10 shows a cross-sectional view of the expandable fusion device expanded in lordosis;

FIG. 11 shows a side view of the expandable fusion device expanded in lordosis;

FIG. 12 shows a back view of the expandable fusion device expanded in lordosis;

FIG. 13 shows a perspective view of the expandable fusion device expanded in lordosis

DETAILED DESCRIPTION OF THE INVENTION

The goal of spinal fusion surgery is fusion of the two vertebrae adjacent to the targeted disc level, often done through an interbody cage procedure. The endplates of the implant come into contact with the patient's vertebral endplates to thereby promote fusion. Implantation of intervertebral spacers from a posterior approach requires surgeons to be aware of nerve roots and other anatomy as they pass a spacer into the disc space. The posterior margin is smaller than the anterior margin of the disc space so in order to insert a static spacer to fit the anterior space, a spacer larger than the posterior space may need to be inserted potentially causing damage during insertion. An expandable spacer implant is able to start out small so it can be passed through the posterior margin and then expanded to get endplate to endplate fit in the anterior aspect of the disc space. Access to the disc space may require some type of inserter instrumentation rigidly affixed to the implant that can be detached from the implant when required. Accordingly, embodiments of the present application are generally directed to devices, systems, instruments, and methods for installing and expanding the implant.

Figure 1:
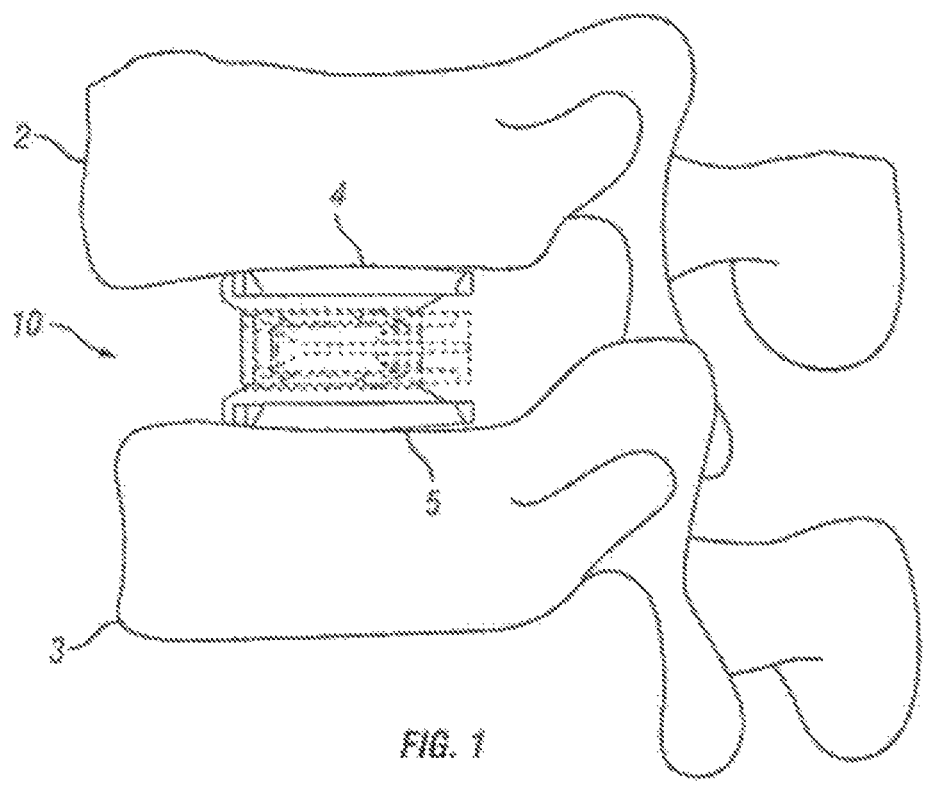
FIG. 1 is a side view of an expandable fusion device shown between two adjacent vertebrae.

A spinal fusion is typically employed to eliminate pain caused by the motion of degenerated disc material. Upon successful fusion, a fusion device becomes permanently fixed within the intervertebral disc space. Looking at FIG. 1, an expandable fusion device 10 is shown between adjacent vertebral bodies 2 and 3. The fusion device 10 engages the endplates 4 and 5 of the adjacent vertebral bodies 2 and 3 and, in the installed position, maintains normal intervertebral disc spacing and restores spinal stability, thereby facilitating an intervertebral fusion. The expandable fusion device 10 can be manufactured from a number of materials including titanium, stainless steel, titanium alloys, non-titanium metallic alloys, polymeric materials, plastics, plastic composites, PEEK, ceramic, and elastic materials. In an embodiment, the expandable fusion device 10 can be configured to be placed down an endoscopic tube and into the disc space between the adjacent vertebral bodies 2 and 3.

In an exemplary embodiment, bone graft or similar bone growth inducing material can be introduced around and within the fusion device 10 to further promote and facilitate the intervertebral fusion. The fusion device 10, in one embodiment, is preferably packed with bone graft or similar bone growth inducing material to promote the growth of bone through and around the fusion device. Such bone graft may be packed between the endplates of the adjacent vertebral bodies prior to, subsequent to, or during implantation of the fusion device. The terms implant, fusion device, spacer, and expandable device may be used interchangeably herein.

Referring now to FIGS. 2-5, an embodiment of the fusion device 10 is shown. In an exemplary embodiment, the expandable fusion device 10 comprises a first or lower endplate 20, a second or upper endplate 30, a housing or body 40 positioned between the first endplate 20 and the second endplate 30, a nose 50, a drive screw 60, a friction ring or washer 70, a locking ring or lock 80, and a retaining ring 90. The endplates 20, 30 may have two main pairs of ramps that allow for expansion: two back ramps that mate with the two ramps of the body 40, and two front ramps that mate with the ramps of the nose 50. The drive screw 60 advantageously provides a threaded mechanism for expanding and contracting the expandable fusion device 10. The drive screw 60 may be mated with washer 70 to reduce expansion force and/or add friction to the drive screw 60 while being seated inside the body 40 and threaded into the nose 50. The lock 80 may be used to eliminate rotation to the drive screw 60 while the retaining ring 90 may retain the drive screw 60, lock 80, and/or retaining ring 90 in the body 40. To expand the implant 10, the drive screw 60 is rotated pulling the nose 50 towards the body 40 and causing the endplates 20, 30 to ride up the ramps of the body 40 and nose 50. When this happens, the implant 10 first expands in lordosis (shown in FIG. 3) and then expands in height (shown in FIG. 4). The expandable device 10 may include the same or similar features to any of the expandable devices described in U.S. Patent Publication No. 2017/0354512, which is hereby incorporated by reference in its entirety for all purposes. In particular, fusion device 10 may include features similar to expandable device 800 shown in U.S. Patent Publication No. 2017/0354512.

Figure 18:
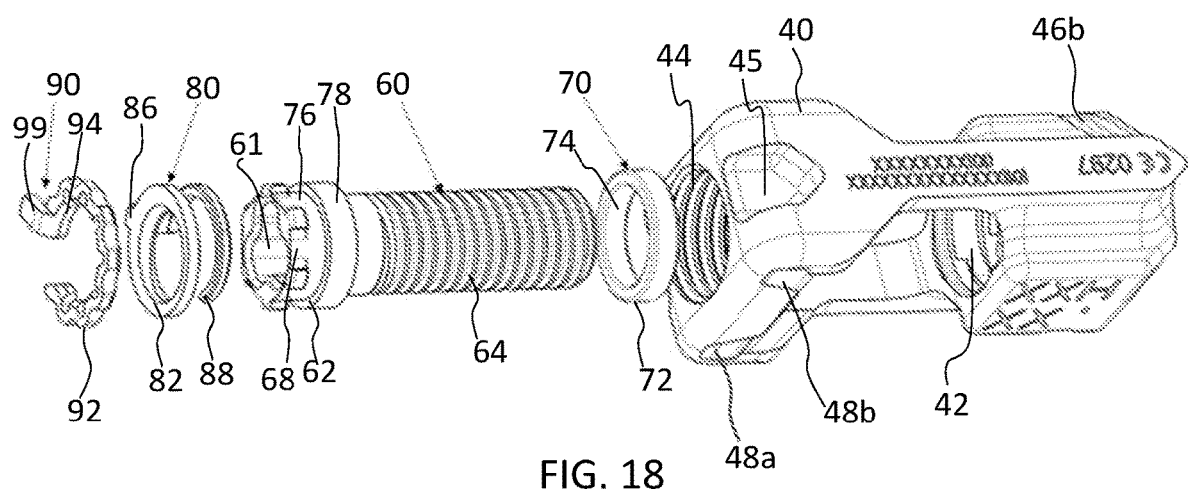
FIG. 18 is an exploded view of the drive screw mechanism according to one embodiment.

The first endplate 20 comprises a lower endplate having a first end 22 and a second end 24. The first endplate 20 comprises one or more ramps or ramped portions configured to engage with the body 40 and/or the nose 50 of the assembled device 10. In one embodiment, the first end 22 comprises a pair of first end ramped portions 26a, 26b. Each of these ramped portions 26a, 26b is configured to engage corresponding lower nose ramps 52a, 52b on the nose 50 to aid with expansion of the expandable fusion device 10. The second end 24 comprises a pair of second end ramped portions 28a, 28b. Each of these ramped portions 28a, 28b is configured to engage corresponding rear lower ramps 48a, 48b (shown in FIG. 18) on the body 40 to aid with expansion of the expandable fusion device 10. The first endplate 20 may include a first central ramp 27a and a second central ramp 27b positioned between the first end 22 and the second end 24 of the first endplate 20. Each of the central ramps 27a, 27b may be configured to engage corresponding front lower ramps 46a, 46b of the body 40 to aid with expansion of the expandable fusion device 10. The ramps of the first endplate 20 are formed along a perimeter that surrounds a central opening 29.

The second endplate 30 may be the same or similar to endplate 20 (e.g., a mirror image). The second endplate 30 comprises an upper endplate having a first end 32 and a second end 34. The second endplate 30 comprises one or more ramps or ramped portions configured to engage with the body 40 and/or the nose 50 of the assembled device 10. The first end 32 comprises a pair of first end ramped portions 36a, 36b. Each of these ramped portions 36a, 36b is configured to engage corresponding upper nose ramps 54a, 54b on the nose 50 to aid with expansion of the expandable fusion device 10. The second end 34 comprises a pair of second end ramped portions 38a, 38b. Each of these ramped portions 38a, 38b is configured to engage corresponding rear upper ramps 48a, 48b on the body 40 to aid with expansion of the expandable fusion device 10. The endplate 30 may include a first central ramp 37a and a second central ramp 37b positioned between the first end 32 and the second end 34 of the first endplate 30. Each of the central ramps 37a, 37b may be configured to engage corresponding front upper ramps 46a, 46b of the body 40 to aid with expansion of the expandable fusion device 10. The ramps of the second endplate 30 are formed along a perimeter that surrounds a central opening 39.

The housing or body 40 extends from a first end to a second end and comprises a front through bore 42 and a rear through bore 44. The front through bore 42 comprises an opening through which the threaded shaft 64 of the drive screw 60 extends therethrough. The rear through bore 44 comprises an opening through which the head 62 of the drive screw 60 extends therethrough. The rear through bore 44 also receives the washer 70, the retaining ring 80, and/or lock 90 therein. The retaining ring 90 may be received in a recess of the head 62, which is then received in the rear through bore 44. In some embodiments, the retaining ring 90 comprises a c-shaped ring.

The drive screw 60 comprises a head portion 62 and a shaft portion 64. The head portion 62 comprises a recess or opening 61 for receiving an instrument, such as a driver or expansion tool (e.g., driver 116). The opening 61 may include a tri-wing configuration with three evenly spaced slots, but the opening 61 could also be slotted, Phillips, torx, hex, square, or of any other suitable configuration. The head portion 62 may comprise a recess 76 for receiving the lock 80. The head portion 62 can be received in the rear through bore 44 of the body 40. The shaft portion 64 comprises a threaded portion that extends through the nose 50. The threaded portion mates with threads 56 within the nose 50. Rotation of the drive screw 60 thereby causes movement or translation of the nose 50.

In some embodiments, one or more tools (e.g., an expansion tool) can engage the head 62 of the drive screw 60. Rotation of the drive screw 60 in a first direction translates and draws the nose 50 inwardly, thereby causing expansion between the first endplate 20 and the second endplate 30. As the nose 50 is drawn inwardly, upper nose ramps 54a, 54b engage first end ramped portions 36a, 36b of the second endplate 30, while rear upper ramps 48a, 48b of the body 40 engage second end ramped portions 38a, 38b of the second endplate 30. Likewise, lower nose ramps 52a, 52b engage first end ramped portions 26a, 26b of the first endplate 20, while rear lower ramps engage second end ramped portions 28a, 28b of the first endplate 20. The engagement of these ramps causes outward expansion between the first endplate 20 and the second endplate 30. Rotation of the drive screw 60 in a second direction opposite to the first direction translates the nose 50 outwardly, thereby causing contraction between the first endplate 20 and the second endplate 30.

The nose 50 comprises a through hole 58 through which the shaft portion 64 of the drive screw 60 can extend. The through hole 58 of the nose 50 comprises nose threads 56 that engage and mate with the threads of the shaft portion 64. As noted above, the nose 50 comprises one or more upper nose ramps 54a, 54b, which are configured to mate and engage corresponding ramps on the second endplate 30. In addition, the nose 50 comprises one or more lower nose ramps 52a, 52b, which are configured to mate and engage corresponding ramps on the first endplate 20.

Figure 2:
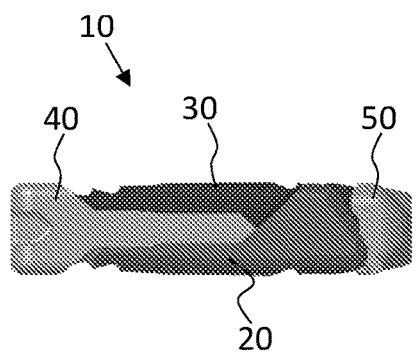
FIG. 2 shows a side view of an expandable fusion device according to one embodiment in a contracted position.
Figure 3:
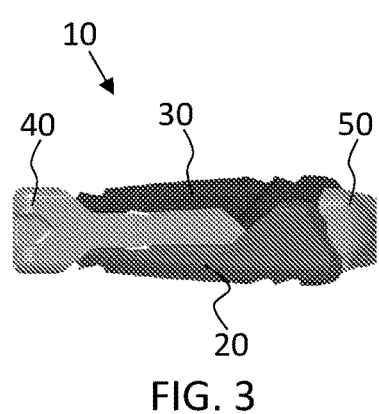
FIG. 3 shows a side view of the expandable fusion device of FIG. 2 expanded in lordosis.
Figure 4:
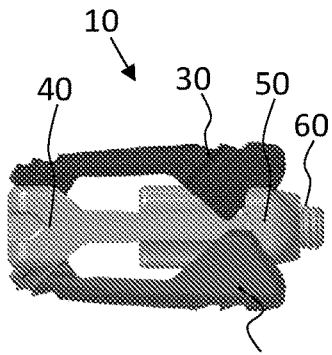
FIG. 4 shows a side view of the expandable fusion device of FIG. 3 expanded in height.
Figure 5:
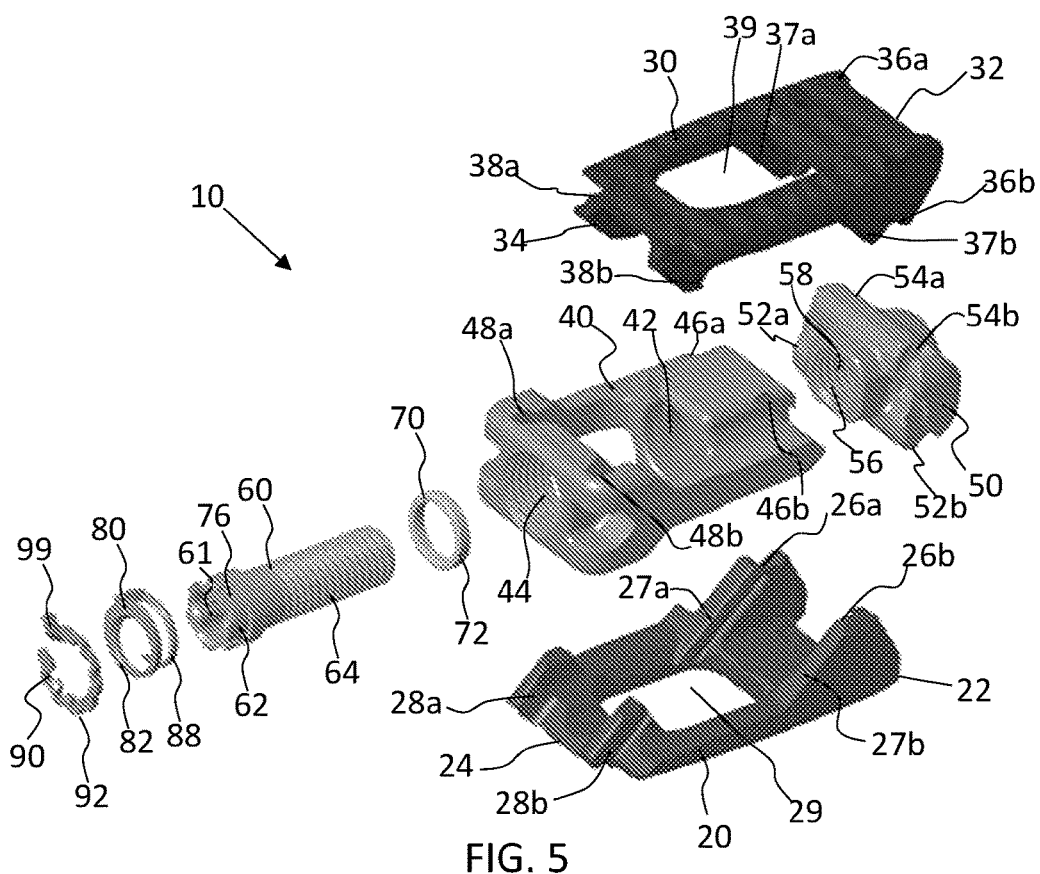
FIG. 5 is an exploded view of the expandable fusion device of FIGS. 2-4.
Figure 14:
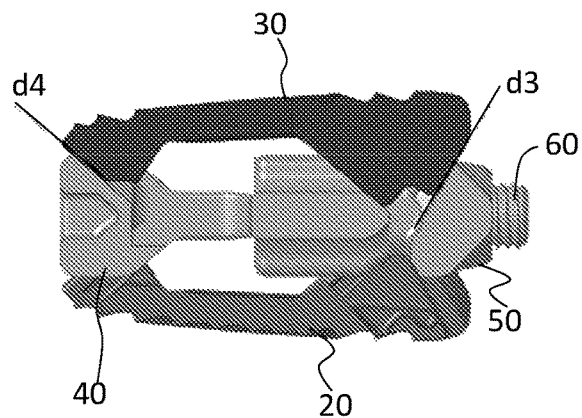
FIG. 14 shows a cross-sectional view of the expandable fusion device at the expanded height.
Figure 15:
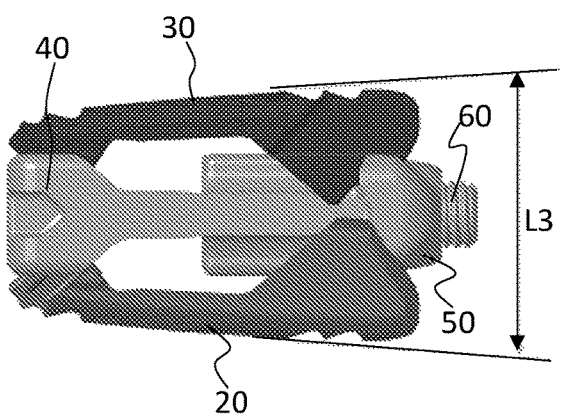
FIG. 15 show a side view of the expandable fusion device at the expanded height.
Figure 16:
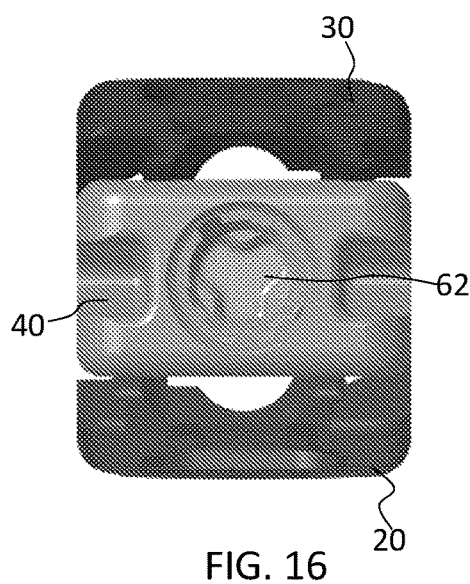
FIG. 16 is a back view of the expandable fusion device at the expanded height.
Figure 17:
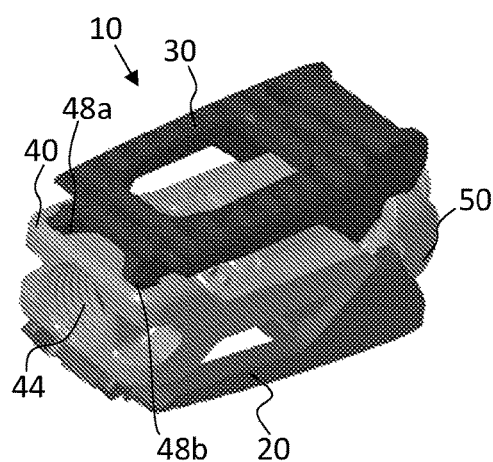
FIG. 17 is a perspective view of the expandable fusion device at the expanded height.

FIGS. 2-4 are side views of the expandable fusion device 10 of FIG. 5 in the process of expansion in accordance with some embodiments. In some embodiments, the expandable fusion device 10 is advantageously capable of expansion, and in particular, lordotic expansion. In some embodiments, the device 100 can begin in a contracted state, as shown in FIG. 2. Afterwards, by pulling the nose 50 via rotation of the drive screw 60, the device 10 can expand and tip into lordosis, as shown in FIG. 3. Once the device 10 has achieved maximum lordosis, the device 10 can continue to expand in height in a parallel fashion, whereby both the anterior and posterior aspects expand at the same rate, until the implant 10 reaches a maximum expansion, as shown in FIG. 4. In other words, once the device 10 reaches a particular lordotic angle (as shown in FIG. 3), the device 10 will maintain the lordotic angle throughout the expansion range until maximum expansion has been achieved, as shown in FIG. 4.

Turning to FIGS. 6-9, the contracted position of the implant 10 is shown. The lordotic growth is driven by a difference in ramp angle d1, d2. As best seen in FIG. 6, a difference in ramp angle d1 is seen between the front endplate ramp 36a, 36b and the nose ramp 54a, 54b. A difference in ramp angle d2 is seen between the back endplate ramp 38a, 38b and body ramp 48a, 48b. For example, the differences d1, d2 may range from about 1-5°, or about 3°. Although shown for endplate 30 it will be appreciated that the same or similar difference in ramp angles d1, d2 may be provided for endplate 20 as well. As best seen in FIG. 7, in the contracted height, the difference in angle d1, d2 causes the implant 10 to be in a lesser lordotic state L1. In other words, even when fully contracted, the upper and lower endplates 20, 30 may provide a mild lordotic height L1 of about 1-5°, or about 2° for the implant 10.

Turning now to FIGS. 10-13, the implant 10 is expanded in lordosis. Once the implant 10 begins to expand, the nose 50 is pulled back causing the angle difference d3, d4 to go to zero as the front ramp 36a, 36b of the endplate 30 begins to mate with ramp 54a, 54b of the nose 50. For example, the difference in ramp angle d3 between the front endplate ramp 36a, 36b and the nose ramp 54a, 54b is now zero, and the difference in ramp angle d4 between the back endplate ramp 38a, 38b and body ramp 48a, 48b is also zero. As this happens, the back ramps 38a, 38b of the endplate 30 are forced to mate with the ramps 48a, 48b in the body 40. Once the ramps are all at the same angle, the implant 10 is now in its lordotic expanded state L2. In other words, when expanded in lordosis, the upper and lower endplates 20, 30 may provide a lordotic angle L2 of about 1-10°, about 4-8°, or about 8° for the implant 10. There has been no expansion in the back at this point, just the front causing the lordotic angle L2 seen in FIG. 11. The total lordosis is controlled by the difference in ramp angle d1, d2 in the contracted state. For example, if the ramp angle difference is 3° for each endplate 20, 30, the total change of lordosis when expanded is 6° (two endplates 20, 30 at 3° equals 6° total change for the implant 10).

Turning now to FIGS. 14-17, the implant 10 is fully expanded in height with the lordosis L3. As the implant 10 continues to expand and the front nose 50 is pulled back more, the implant 10 expands in a parallel fashion (anterior and posterior grow at the same rate) because the ramps are now at the same angle and are forced to consistently translate up the ramp at that angle. For example, the difference in ramp angle d3 between the front endplate ramp 36a, 36b and the nose ramp 54a, 54b is maintained at zero, and the difference in ramp angle d4 between the back endplate ramp 38a, 38b and body ramp 48a, 48b is also maintained at zero. This causes the implant 10 to maintain lordosis but grow in overall height. In other words, when expanded in height, the upper and lower endplates 20, 30 may provide a lordotic angle L3 (e.g., 8°) equal to lordotic angle L2 (e.g., 8°), but with a greater overall height of the implant 10. Height expansion stops when the nose 50 bottoms out on the body 40.

In some embodiments, the device 10 can be used via different approaches. For example, in some embodiments, the device 10 can be a TLIF device that enters a disc space via a transforaminal approach, while in other embodiments, the device 10 can be a PLIF device that enters a disc space via a posterior approach. In other embodiments, the device 10 can be an ALIF device that enters via an anterior approach. One skilled in the art will appreciate that the device 10 is not limited to any particular approach.

Figure 19:
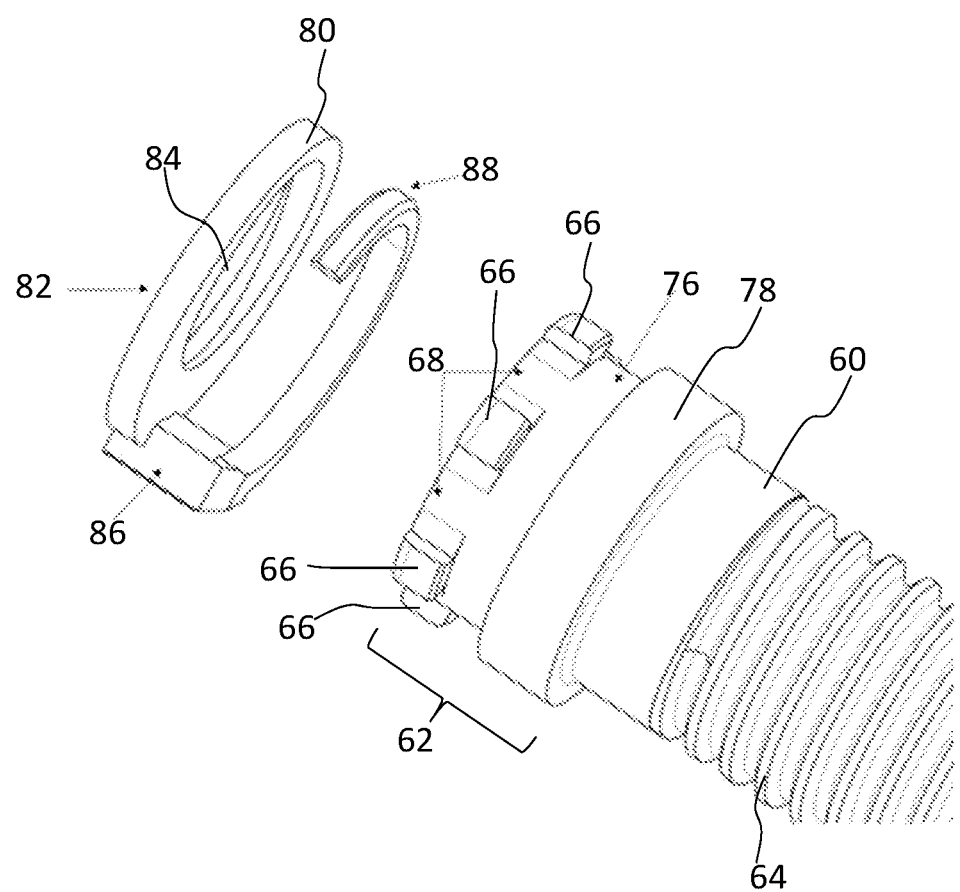
FIG. 19 is a close-up exploded view of the drive screw and locking ring shown in FIG. 18.
Figure 20:
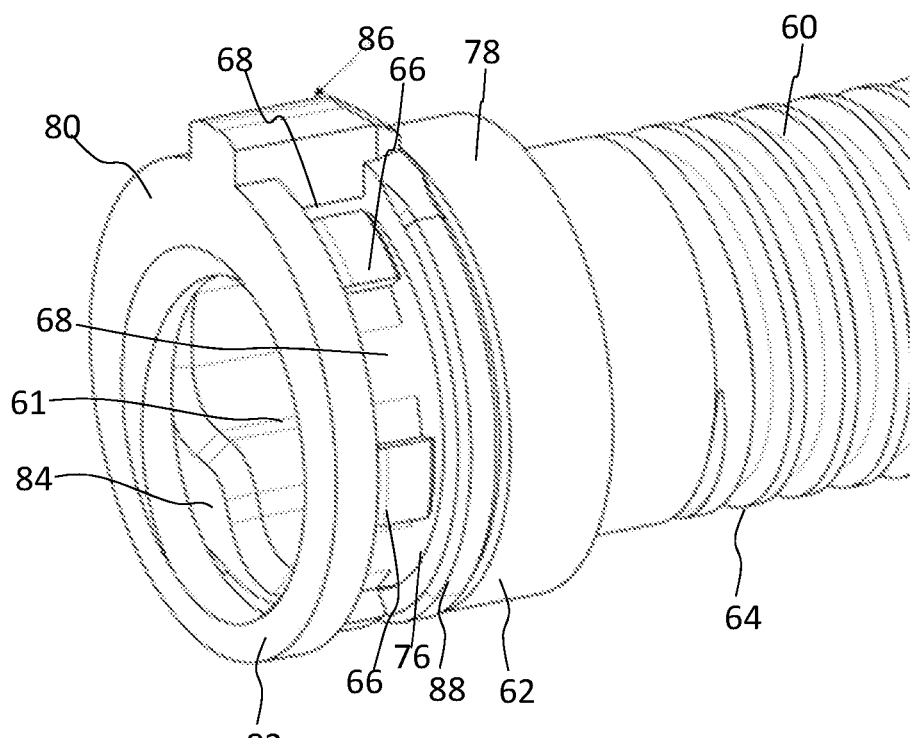
FIG. 20 is a close-up assembled view of the drive screw and locking ring shown in FIG. 18.

Turning now to FIGS. 18-21, the drive screw assembly is provided in more detail. In particular, the housing or body 40, drive screw 60, friction ring or washer 70, locking ring or lock 80, and retaining ring 90 of the implant 10 are shown, but the endplates 20, 30 are omitted for clarity. The drive screw 60 comprises head portion 62 and shaft portion 64. The shaft portion 64 may be partially or fully threaded along its length. A close-up view of the head portion 62 is shown in FIG. 19. The head portion 62 has a plurality of protrusions 66 separated by a plurality of notches 68 located radially around the tip of the head portion 62 with a circumferential groove 76 behind the notches 68. The protrusions 66 may include a plurality of equidistantly spaced projections, thereby creating the plurality of equidistantly spaced notches 68. The protrusions 66 may include quadrilateral projections, such as square or rectangular protrusions, thereby forming generally quadrilateral notches 68 therebetween. Although it is envisioned that any suitable number, type, and shape of protrusions 66 and notches 68 may be selected. The circumferential groove 76 may be positioned between the protrusions 66 and an annular ring 78.

The friction ring or washer 70 may be an annular ring having an outer surface 72 configured to contact the body 40 and an inner surface 74 configured to contact the drive screw 60, for example, below the annular ring 78 of the drive screw 60. The friction ring or washer 70 may or may not be included in the assembly. When present, the optional friction ring 70 may help to reduce expansion force and/or add friction to the drive screw 60 while being seated inside the body 40 and the drive screw 60 is threaded into the nose 50 of the device 10.

As best seen in FIG. 19, the locking ring or lock 80 may include a first ring 82 and a second ring 88 connected by a strut 86. The lock 80 may be shaped such that the top portion is a full ring 82 with a central through hole 84 off center of the outer geometry. In other words, the through hole 84 is not aligned with the central longitudinal axis of the drive screw 60. The ring 82 connects with the strut 86 to a lower C-shaped spring ring 88. The strut 86 may have a thickness greater than the thickness of the first or second rings 82, 88. As best seen in in FIG. 20, the lock 80 is first inserted onto the screw head 62 such that the C-ring 88 rests in the circumferential groove 76 of the screw head 62 and the strut 86 is located in one of the notches 68. The top ring 82 of the lock 80 rests on a top face of the screw head 62. The offset opening 84 is partially aligned with the opening 61 in the head portion 62 of the screw 60.

Figure 21:
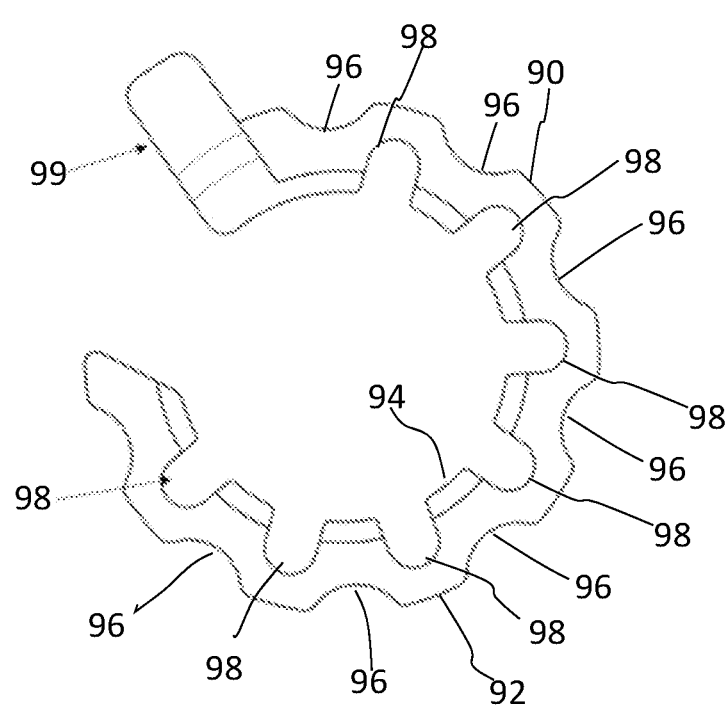
FIG. 21 is a close-up side view of the retaining ring of FIG. 18.

As best seen in FIG. 21, the retaining ring 90 has a generally C-shaped body and includes an outer surface 92 configured to contact the body 40 and an inner surface 94. The retaining ring 90 may include a plurality of outer radial notches 96 and/or a plurality of inner radial notches 98 that allow the ring 90 to deflect without deforming. The outer and inner radial notches 96, 98 may include arcuate cutouts. The notches 96, 98 may be equidistantly spaced around the outer and inner surfaces 92, 94, respectively. As shown, the depth of the inner notches 98 may be deeper than the depth of the outer notches 96. The notches 96, 98 may also alternate with an inner notch 98 separating each pair of outer notches 96. Although it is envisioned that the number, location, and depth of the notches 96, 98 may be selected to provide the desired amount of deflection. The retaining ring 90 may include a tab 99 to allow the retaining ring 90 to be removed if desired. The tab 99 may be elongated to protrude outwardly past the outer surface 92 of the ring 90. The retaining ring 99 may be placed in the housing 40 behind the drive screw assembly to prevent it from disassembling.

Figure 22:
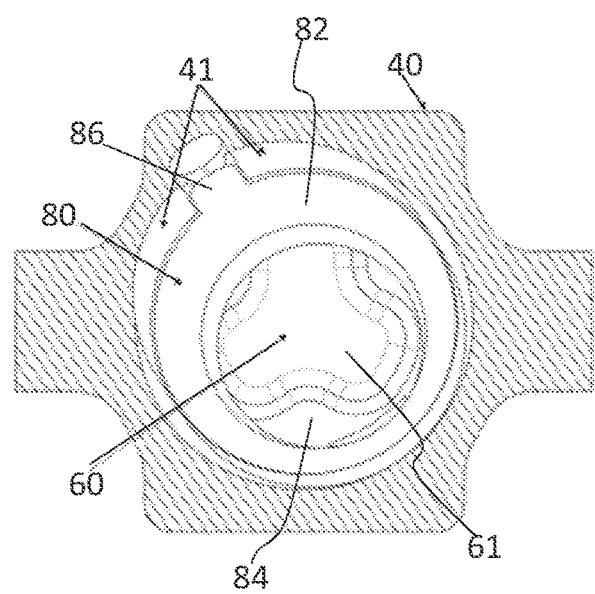
FIG. 22 is a cross-sectional view of the housing viewing the top of the lock and drive screw assembly providing clearance for the lock to translate.
Figure 23:
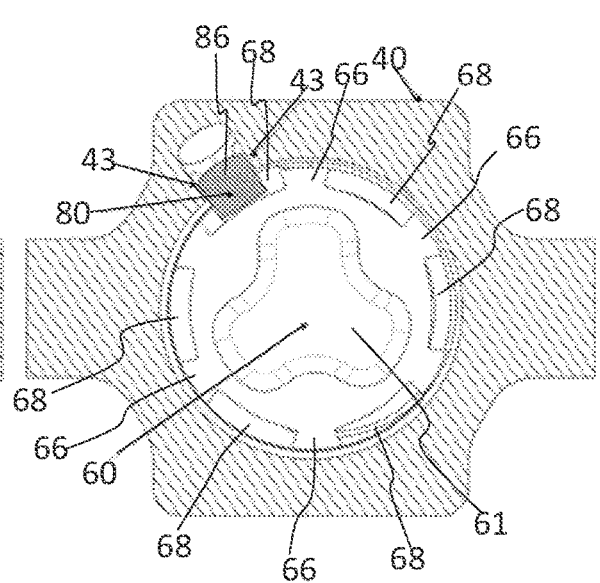
FIG. 23 is a cross-sectional view of the housing and drive screw assembly showing restriction of rotation of the lock and the screw.

As best seen in FIGS. 22 and 23, the drive screw assembly is oriented and inserted into the housing 40. As shown in FIG. 22, the housing 40 is designed such that there may be a clearance 41 for the lock 80 to translate in the housing 40. In other words, the housing 40 may have a gap or recess dimensioned slightly larger than the outer surface of the lock 80 to allow for translation of the lock 80. As shown in FIG. 23, the housing 40 may be also dimensioned to restrict the lock 80 from rotating within the housing 40. In other words, the housing 50 may have an opening or recess 43 dimensioned substantially the same as the outer dimension of the strut 86, such that the lock 80 is unable to rotate. In this way, when the lock strut 86 is located in one of the screw notches 68, the screw 60 is unable to rotate relative to the housing 40 since the lock 80 cannot rotate about the screw 60 and the lock 80 cannot rotate within the housing 40.

Figures 24, 25:
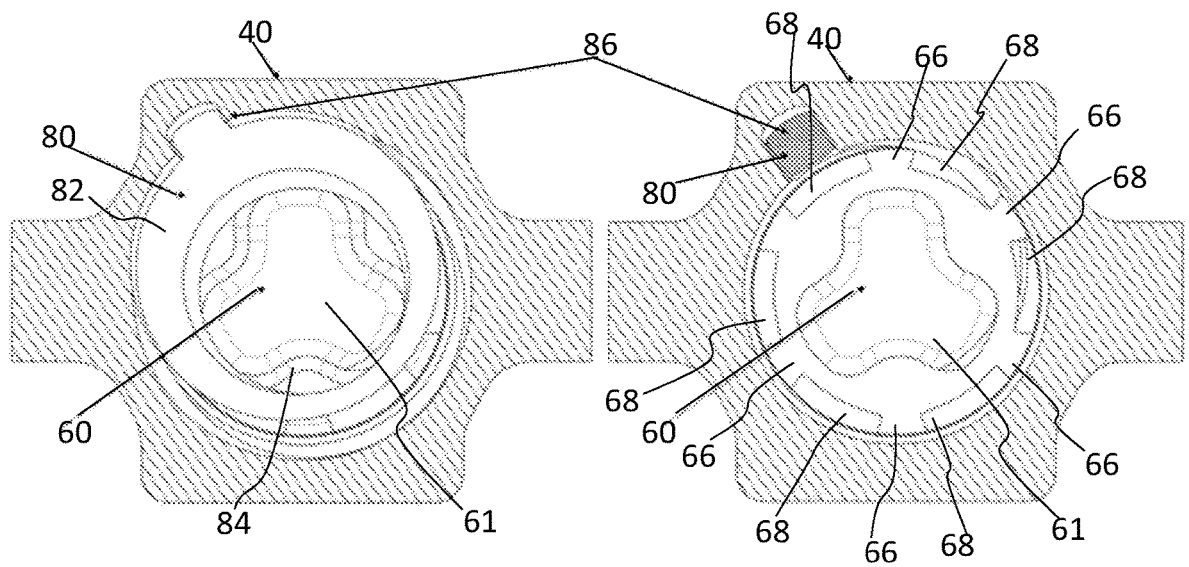
FIG. 24 is a cross-sectional view of the housing viewing the top of the lock and drive screw assembly showing the lock in an unlocked position.
FIG. 25 is a cross-sectional view of the housing and drive screw assembly showing the lock in an unlocked position.

With emphasis on FIGS. 24 and 25, an unlocked position for lock 80 in housing 40 is shown. To unlock the assembly, a driver (e.g., driver 116) of the same internal shape of the screw opening 61 is inserted into the screw 60. During insertion, the driver will pass through the offset through hole 84 in the lock 80 and translate the lock 80 out of the groove 76 in the screw 60. The strut 86 is translated out of the recess 68 in the screw head 62 and is received in a recess in the housing 40. This allows the screw 60 to freely rotate with respect to the lock 80. Thus, the drive screw 60 is rotatable to thereby expand or contract the endplates 20, 30.

Figures 26, 27:
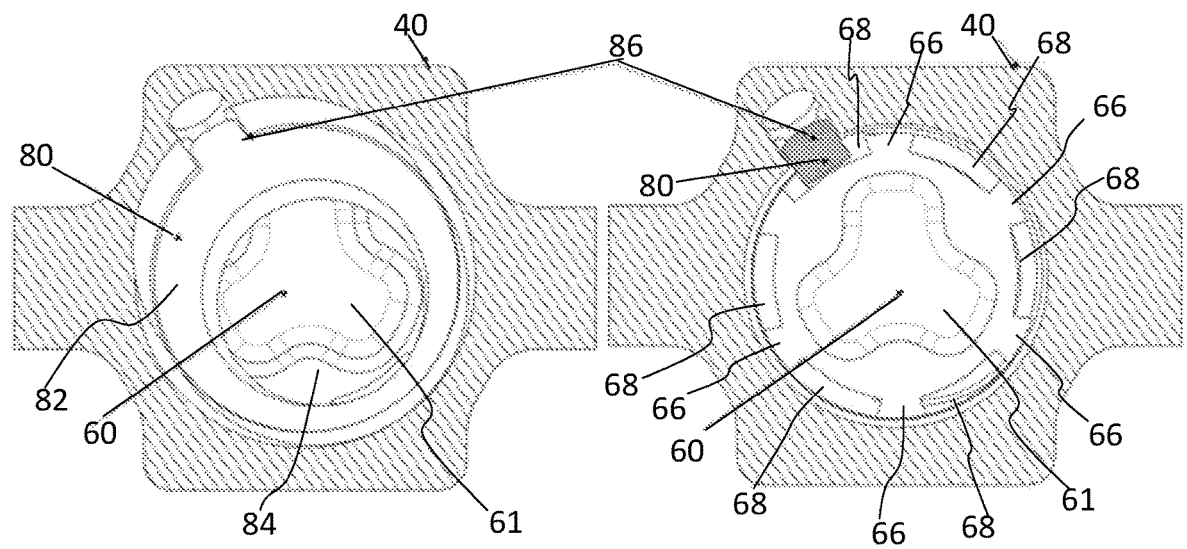
FIG. 26 is a cross-sectional view of the housing viewing the top of the lock and drive screw assembly showing the lock in a locked position.
FIG. 27 is a cross-sectional view of the housing and drive screw assembly showing the lock in a locked position.

With emphasis on FIGS. 26 and 27, a locked position for lock 80 in housing 40 is shown. Once the driver is removed, the C-ring section 88 of the lock 80 will draw the lock 80 back into a locked position, with the lock strut 86 engaged with one of the screw notches 68 and the ring 88 positioned within the recess 76 of the head 62. In the locked position, the screw 60 is unable to rotate and the implant 10 cannot be expanded or contracted.

Figure 28:
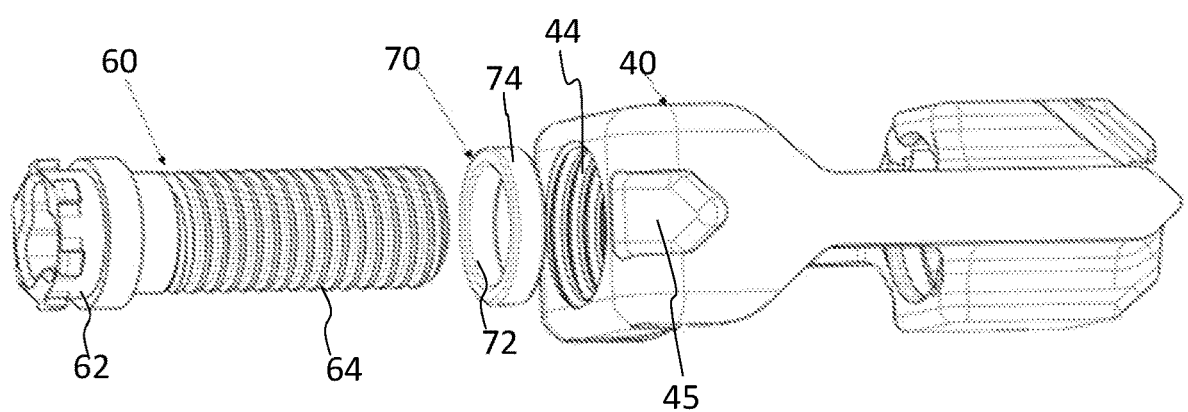
FIG. 28 is an exploded view of a drive screw assembly with a friction ring according to one embodiment.
Figure 29:
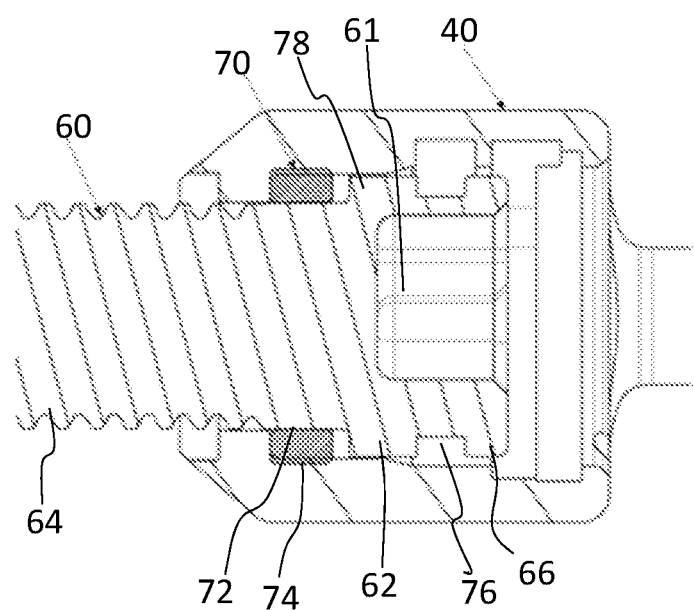
FIG. 29 is a close-up cross-sectional view of the assembly with the friction ring of FIG. 28.

Turning now to FIGS. 28 and 29, a drive screw assembly with a washer or friction ring 70 is shown in greater detail. FIG. 28 provides an exploded view of the body or housing 40, the washer or friction ring 70, and the screw 60. As best seen in the cross-sectional view of FIG. 29, the washer or friction ring 70 is inserted over the shaft 64 of the screw 60 with a tight fit and bottomed out under the screw head 62. In other words, friction ring 70 is positioned on a smooth portion of the shaft 64 under the annular ring 78 and is dimensioned such that it cannot pass the annular ring 78. This assembly may be inserted into the housing 40 in a location that radially compresses the friction ring 70. The housing 40 may utilize a lead in taper to slowly compress the friction ring 70 so that the ring 70 remains intact and does not peel or become damaged. The friction ring 70 may act in two ways, for example. First, the compressed fit provides resistance to the rotating screw 60 in the form of friction. Therefore, depending on the extent of the compression different amounts of torque may be required to overcome the static friction. Second, the location of the ring 70 under the screw head 62 allows the ring 70 to act as a thrust washer, reducing the likelihood of galling between the metal screw and metal housing when high torques are reached. The friction ring 70 may be made of a suitable material to impart the appropriate friction, such as a plastic, including any variation of PEEK (polyetheretherketone). The ring 70 may be used independently or in conjunction with the other locking designs.

Figure 30:
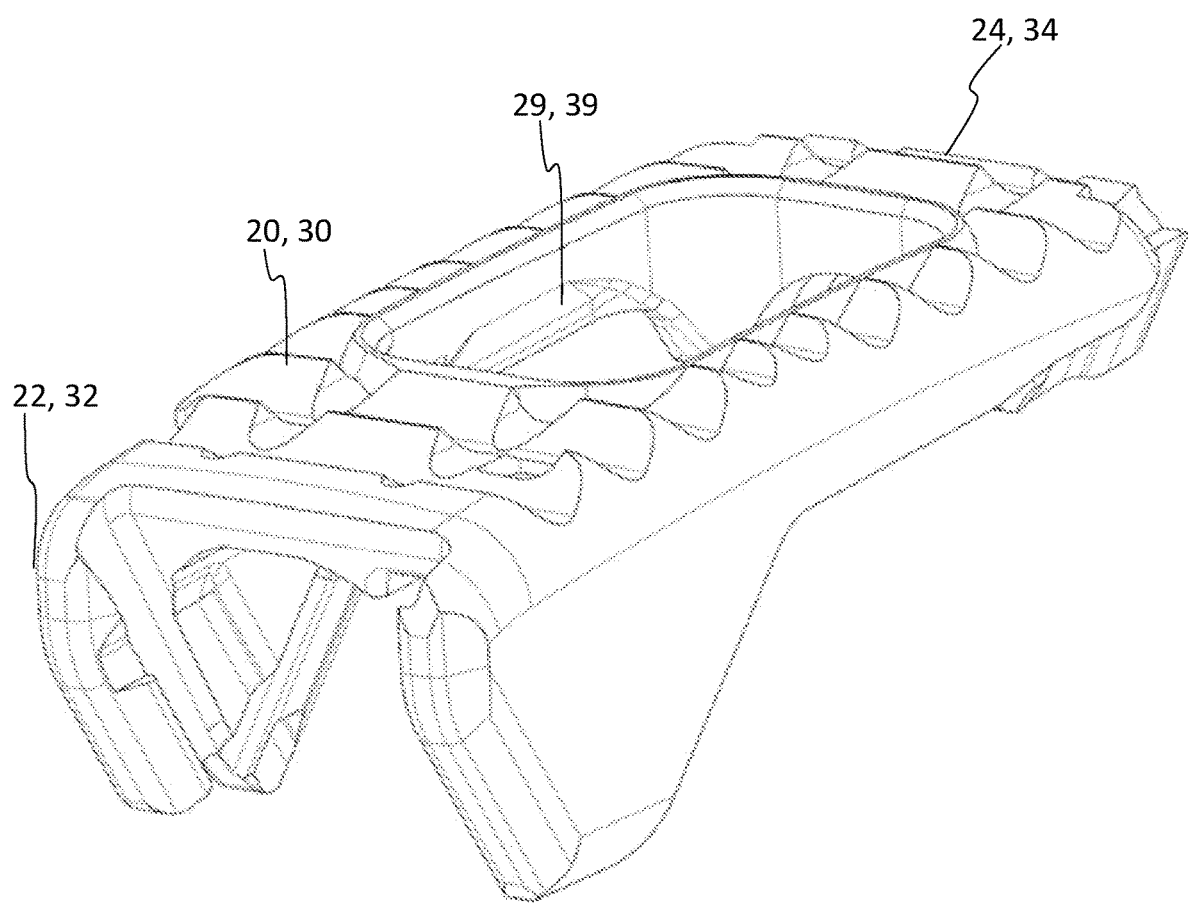
FIG. 30 is a perspective view of an endplate of the expandable fusion device.

With emphasis on FIG. 30, a close-up view of endplate 20, 30 is shown. The endplates 20, 30 may include a plurality of teeth or other surface protrusions configured to engage the adjacent vertebral bodies 2 and 3. The device 10 may also include a roughened and/or porous surface treatment as described in U.S. Publication No. 2017/0354512. The endplates 20, 30 may utilize a 3D printed design which allows for complex geometry to be manufactured with minimal manufacturing time. The 3D printing may also result in surface texturing that can better facilitate bony on growth. For example, any of the 3D printing techniques or designs may be used as exemplified in U.S. Publication No. 2019/0343652, which is incorporated by reference herein in its entirety for all purposes.

Figure 31:
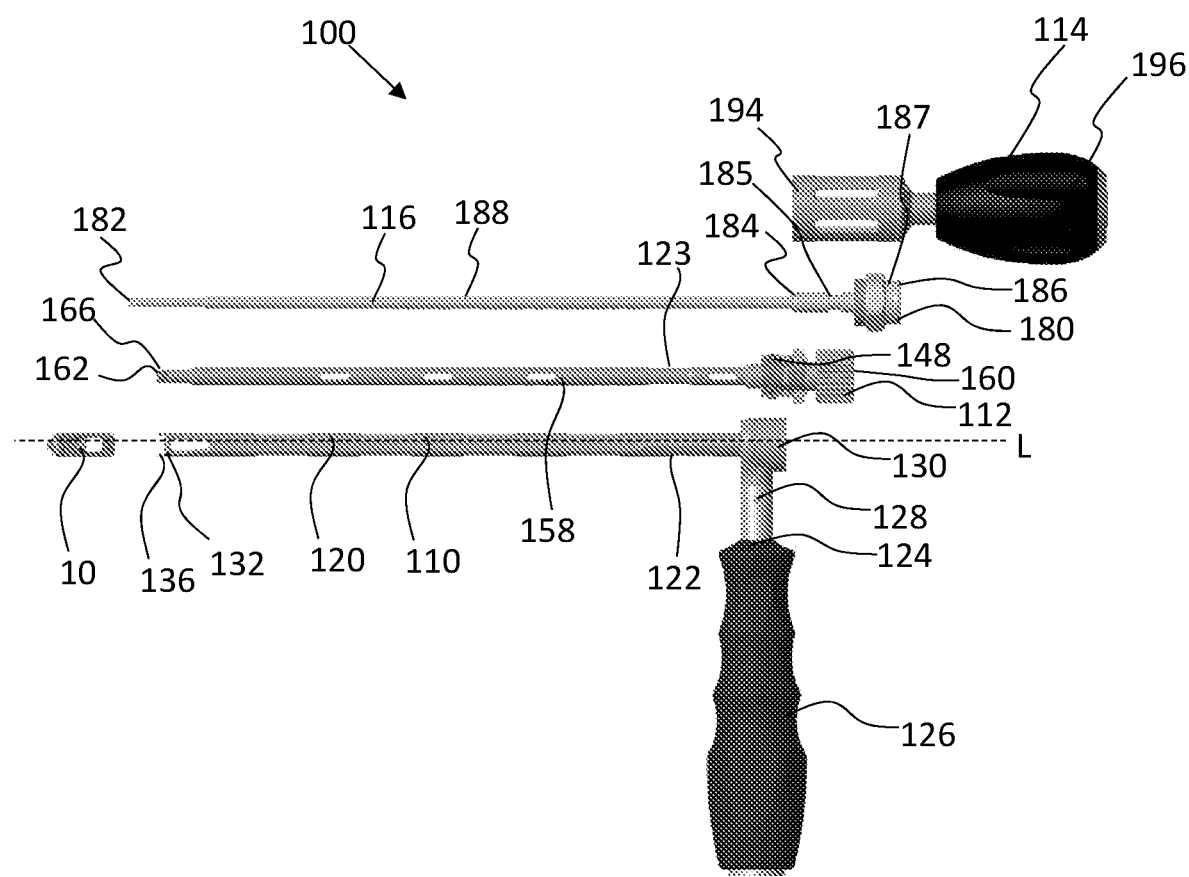
FIG. 31 shows an exploded view of an inserter instrument according to one embodiment.

Turning now to FIG. 31, an inserter instrument 100 may be used to insert and/or expand the implant 10 in the disc space. The inserter 100 may include an inserter sleeve 110, a threaded shaft 112, a drive handle 114, and a driver 116. Each of the primary components serves to ensure that the implant 10 is inserted safely and as intended.

The inserter sleeve 110 may include an inserter body 124 with a guide shaft 120 and a handle 126, a spring tab 122 positioned along the primary axis of the guide shaft 120, and a dowel pin 128 connecting the guide shaft 120 and handle 126. The guide shaft 120 may include a tubular member, hollow tube, or cannula defining a channel 125 therethrough. The guide shaft 120 extends from a proximal end 130 to a distal end 132 along a central longitudinal axis L. The handle 126 may be angled relative to the guide shaft 120, for example, at about 90° relative to the longitudinal axis L of the guide shaft 120.

Figure 32:
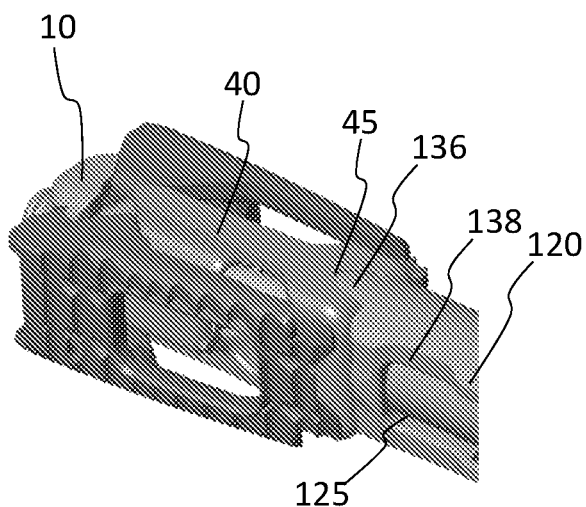
FIG. 32 is a close-up perspective view of the inserter engaged with the expandable fusion device.
Figure 33:
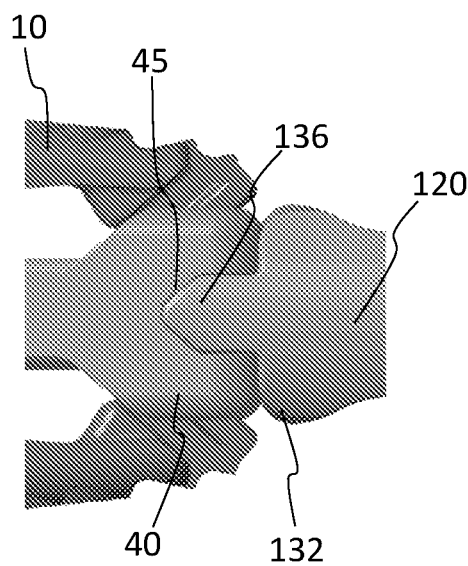
FIG. 33 is a close-up side view of the inserter engaged with the expandable fusion device.

As best seen in FIGS. 32 and 33, one or more tabs 136 may be located on the distal tip 132 of the guide shaft 120. For example, two opposing fixed tabs 136 on the distal tip 132 of the guide shaft 120 may be configured to engage with one or more recesses 45 in the body 40 of the implant 10. The tabs 136 may be sized and dimensioned to mate with the corresponding recesses 45 of the body 40 of the implant 10. The tabs 136 may help to maintain the implant orientation relative to the handle 126 of the inserter 100. The tabs 136 on the distal tip 132 of the guide shaft 120 may be designed with a pointed or angled tip such that the implant 10 is drawn to one orientation or an opposed 180° orientation.

Figure 34:
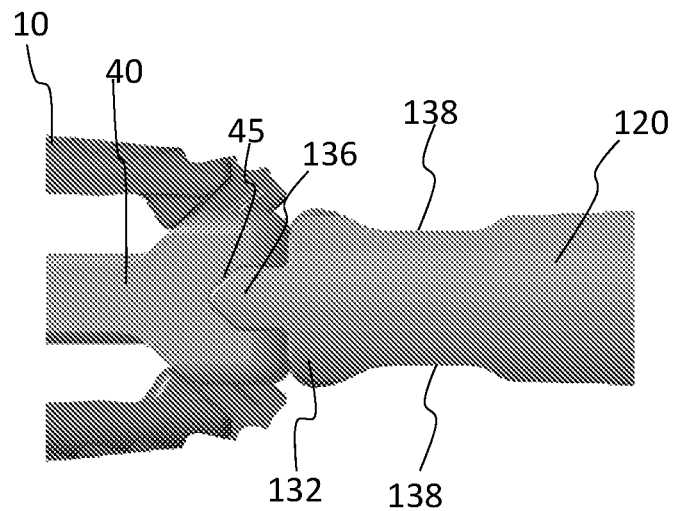
FIG. 34 is a PLIF lateral view of the inserter engaged with the expandable fusion device.
Figure 35:
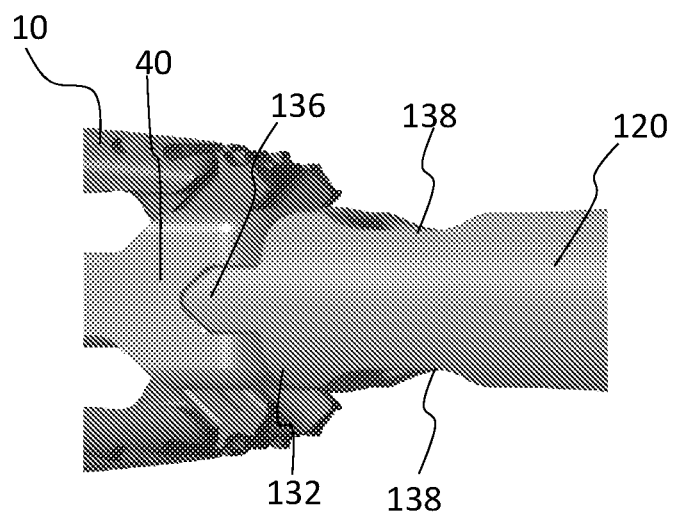
FIG. 35 is a TLIF lateral view of the inserter engaged with the expandable fusion device.

With emphasis on FIGS. 34 and 35, the distal portion 132 of the inserter sleeve 110 may also include one or more groove cuts 138 that allows for a reference to the location of the back of the implant 10 when being viewed under fluoroscopy. The cut or cuts 138 may be made in such a way that as the angle of insertion is changed, the reference point is still visible during fluoroscopy. For example, two opposed cuts 138 may be provided as angled or swept cuts along edges of the guide shaft 120 as shown.

Figure 36:
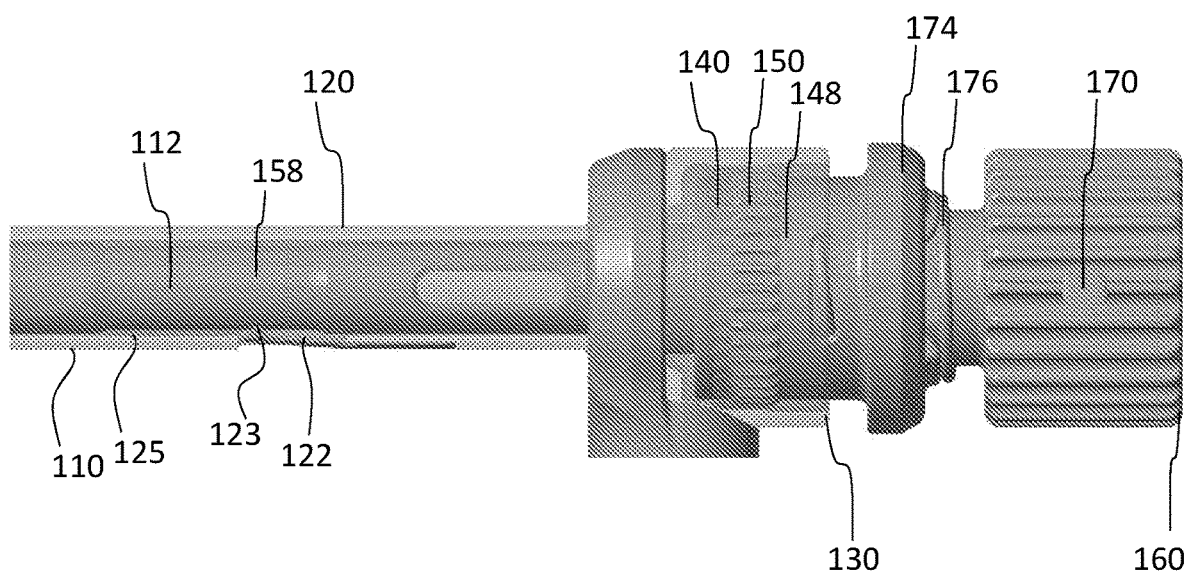
FIG. 36 is a close-up perspective view of the spring tab on the guide shaft of the inserter and the threaded shaft engaged with the guide shaft.

Turning now to FIG. 36, the guide shaft 120 of the inserter sleeve 110 may include a spring tab 122. The spring tab 122 may be positioned along the primary axis of the guide shaft 120. The spring tab 122 may be configured to place spring pressure on a shallow groove 123 on the threaded shaft 112. The spring pressure may be high enough that when the threaded shaft 112 is not threaded into the implant 10, and the inserter 100 is tipped upside-down, the threaded shaft 112 will not fall out of the inserter sleeve 110. Thus, the spring tab 122 retains the threaded shaft 112 within the inner channel 125 of the guide shaft 120.

A plurality of splines 140 may be positioned inside the guide shaft 120 on the proximal side 130 of the inserter sleeve 110. In particular, the proximal end 130 of the guide shaft 120 may have an enlarged portion with the plurality of splines 140 radially positioned about the inner channel 125 of the guide shaft 120. The splines 140 may include a plurality of linear ridges or teeth separated by linear grooves. The splines 140 inside the guide shaft 120 on the proximal side 130 of the inserter sleeve 110 are intended to engage with mating splines 150 on the threaded shaft 112. As shown, the splines 140, 150 may include parallel key splines. It is envisioned, however, that other suitable splines may be selected, such as involute splines, crowned splines, serrations, helical splines, or the like.

The threaded shaft 112 is positionable within the channel 125 of the guide shaft 120 of the inserter sleeve 110. When the threaded shaft 112 and inserter sleeve 110 are engaged (e.g., the splines 140, 150 intermesh), the threaded shaft 112 cannot be rotated and therefore the implant 10 cannot be removed until the splines 140, 150 are disengaged. The engagement of the splines 140, 150 is dependent on whether the driver 116 is connected to the inserter 100 or not as explained in more detail below with reference to the driver 116.

The threaded shaft 112 includes a cannulated connector shaft 158 including an externally threaded portion 166 at its distal tip 162, a spring-loaded button 170 for releasing the driver 116, a spline slider or slider 148 including splines 150, a ring washer, a retaining ring 174, a slider spring 176, and dowel pins 178. The threaded shaft 112 may include a tubular member, hollow tube, or cannula defining a channel 165 therethrough. The threaded shaft 112 extends from a proximal end 160 to a distal end 162 along the central longitudinal axis L.

Figure 37:
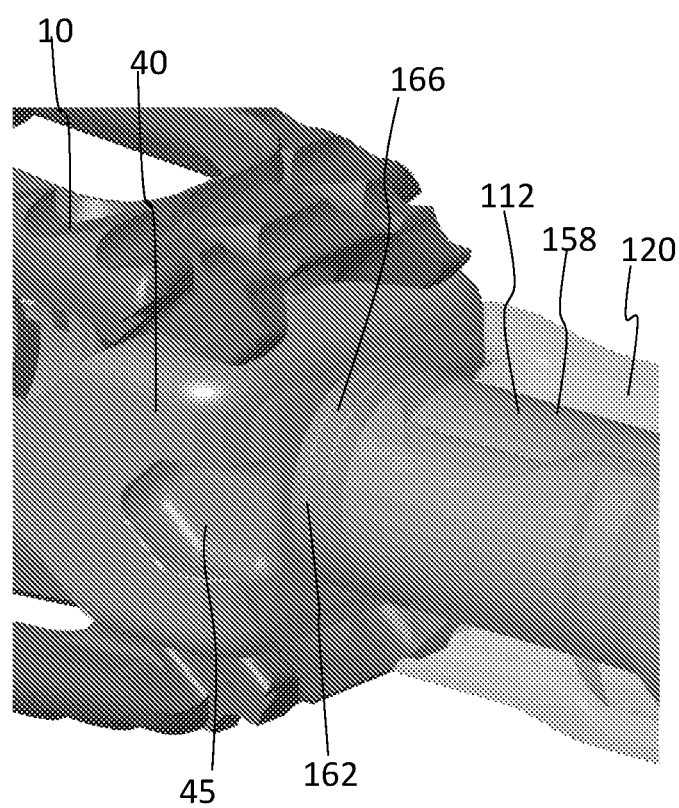
FIG. 37 is a close-up perspective view of the threaded shaft threadedly engaged with the expandable fusion device.

As best seen in FIG. 37, the threaded portion 166 at the distal tip 162 of the threaded shaft 112 includes external threads 166 that directly engage with corresponding threads (e.g., within through bore 44) on the posterior wall of the implant 10. As the threaded portion 166 of the threaded shaft 112 is threaded into the implant 10 (through the guide shaft 120) the implant 10 is drawn into the guide shaft 120 until the orientation tabs 136 align to the implant 10, and then the front of the guide shaft 120 bottoms out on the posterior wall of the implant 10. These threads 166 serve to keep the implant 10 drawn into the inserter 100, and to keep the tabs 136 on the guide shaft 120 engaged with the implant 10. Unlike a splaying fork style inserter prone to having the implant pulled off, the fixed forks 136 and threaded connection 166 may help to ensure that the implant 10 will stay oriented relative to the handle 126 of the inserter sleeve 110, while also ensure that the implant 10 stays secure to the inserter sleeve 110.

Figure 38:
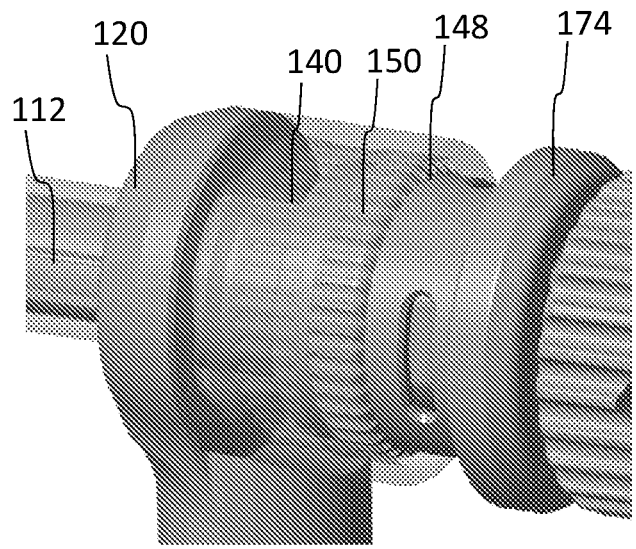
FIG. 38 is a close-up perspective view of the splines inside the guide shaft of the inserter sleeve with the splines of the threaded shaft disengaged.
Figure 39:
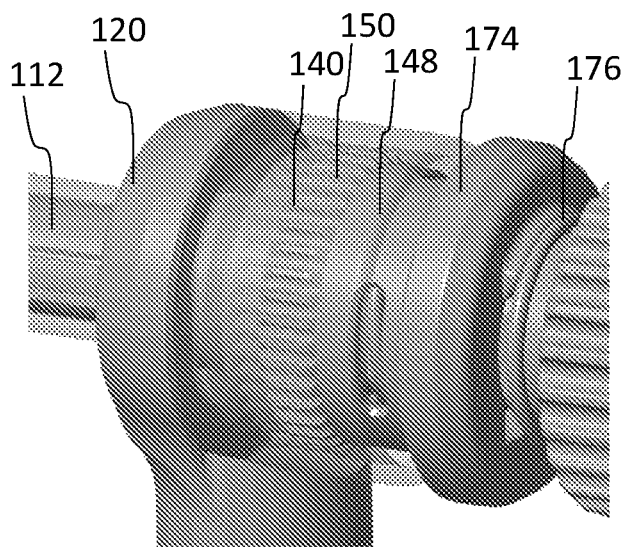
FIG. 39 is a close-up perspective view of the splines inside the guide shaft of the inserter sleeve with the splines of the threaded shaft engaged.
Figure 40:
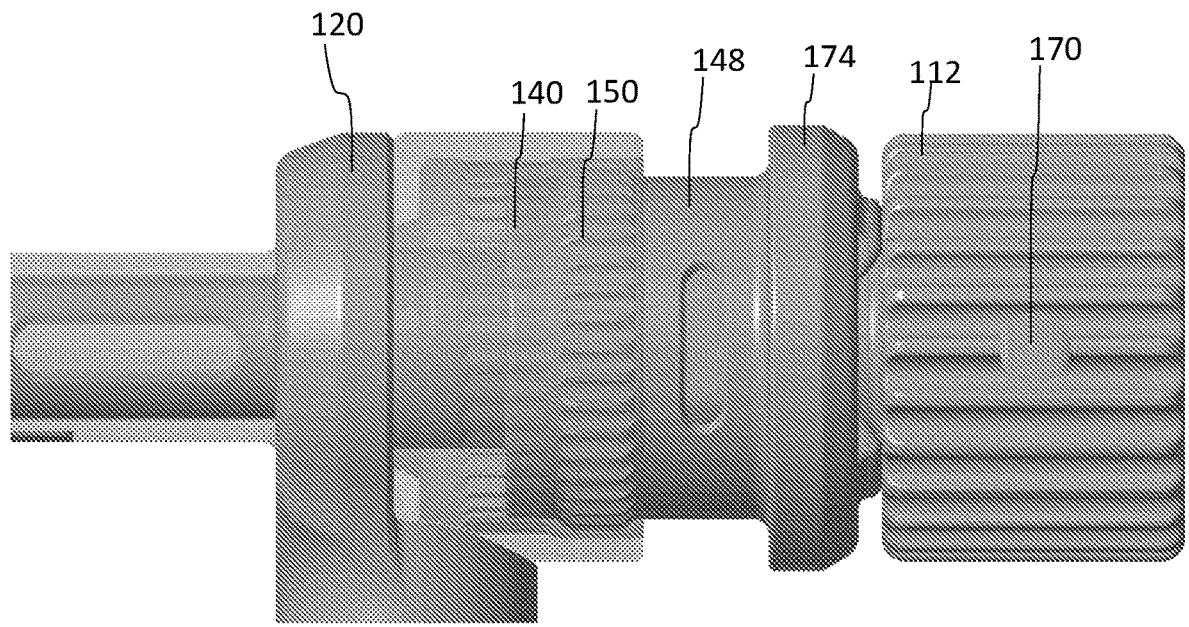
FIG. 40 is a close-up view of the splines inside the guide shaft of the inserter sleeve with the splines of the threaded shaft disengaged.
Figure 41:
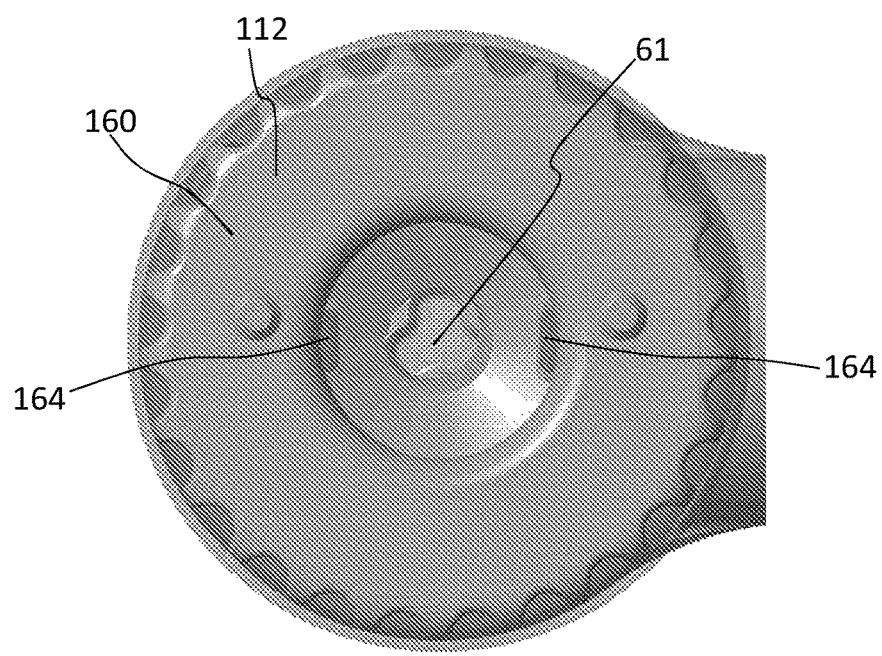
FIG. 41 is a top view of the mechanism that forces the spline slider to engage with the splines on the guide shaft.

Further to FIGS. 38 and 39, the splines 140, 150 are shown in more detail. Often inserters can become disengaged at unexpected and unintended times. The spline engagement features 140, 150 may help to ensure that the implant 10 cannot be disconnected until the driver 116 is removed. As best seen in FIG. 38, the splines 140 of the guide shaft 120 are disengaged from the splines 150 of the threaded shaft 112. In other words, the splines 140, 150 do not intermesh with one another. When the threaded shaft 112 is threaded onto the implant 10 (e.g., via threads 166), the splines 150 on the spline slider 148 are not engaged into the opposing splines 140 of guide shaft 120 (shown in FIG. 38). In this configuration, the threaded shaft 112 could still be turned (e.g., counterclockwise) and removed from the implant 10.

As shown in FIG. 39, the splines 150 on the slider 148 of the threaded shaft 112 engage with the splines 140 on the inside of the guide shaft 120. In other words, the splines 140, 150 are meshed with one another. As the driver 116 is placed through the threaded shaft 112, the driver 116 pushes on the inside of the threaded shaft 112, thereby forcing the spline slider 148 to engage splines 150 with the splines 140 on the guide shaft 120. In particular, the linear cam 184 of the driver 116 may push on engagement members 164 of the threaded shaft 112, thereby linearly translating the spline slider 148 forward and into the engaged positioned shown in FIG. 39. Thus, the slider 148 is configured to slide linearly along the longitudinal axis L towards the distal end 132 of the guide shaft 120, thereby causing the splines 140, 150 to mate (FIG. 39). The slider 148 is also able to slide linearly in the opposite direction along the longitudinal axis L away from the distal end 132 of the guide shaft 120, thereby causing the splines 140, 150 to separate and become disengaged (FIG. 38).

As the driver 116 is advanced and the splines 140, 150 engage, eventually the driver 116 comes into contact with an engagement surface on the button 170 of the threaded shaft 112. The button 170 is spring-loaded such that once the driver 116 is placed far enough, the button 170 engages, and the driver 116 cannot be removed until the button 170 is pressed. Thus, the button 170 retains the driver 116, thereby ensuring that the driver 116 cannot be removed until actively decided by the operator.

Figure 44:
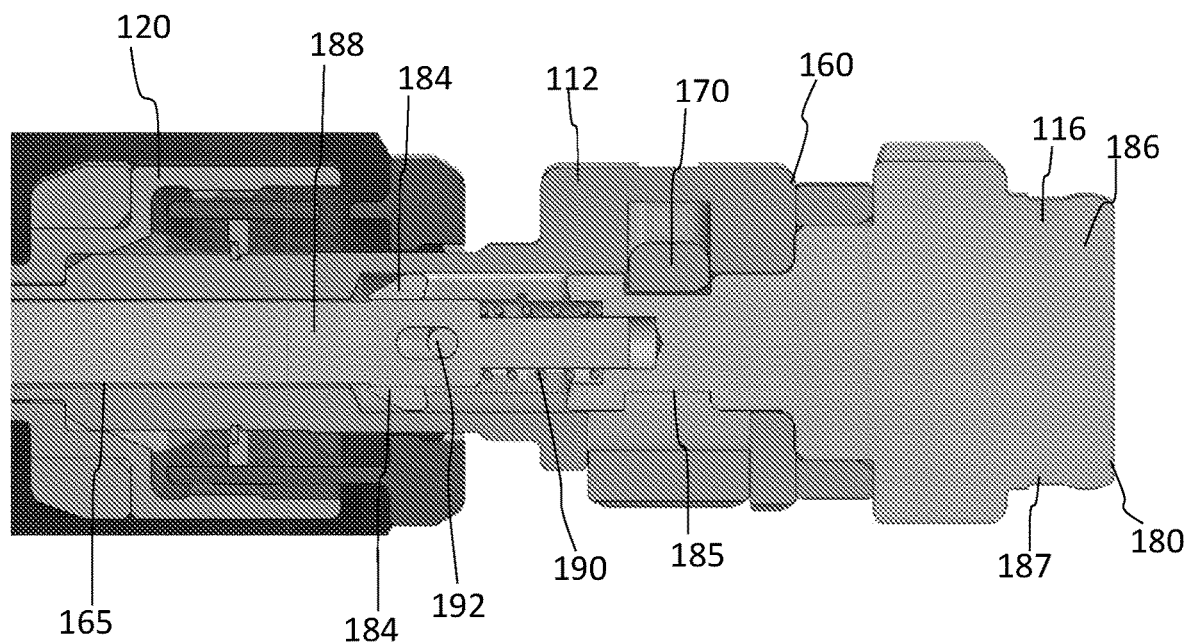
FIG. 44 is a cross-sectional view with the button engaged, and the driver cannot be removed until the button is pressed.
Figure 45:
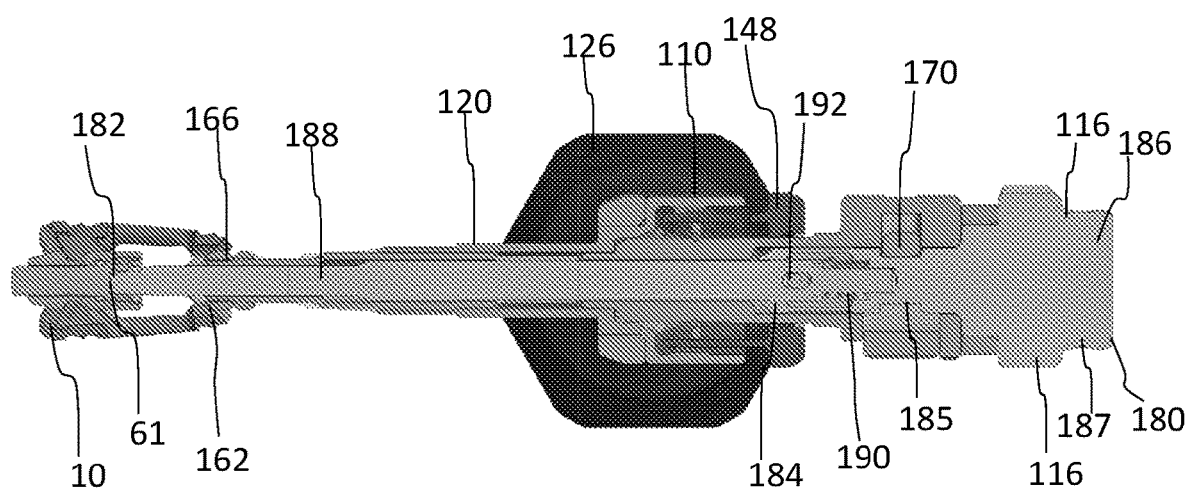
FIG. 45 is a cross-sectional view of the inserter engaged with the expandable fusion device.

With emphasis on FIGS. 44 and 45, the driver 116 includes a driver base 186, a driver shaft 188, a driver shaft spring 190, a dowel pin 192, and a handle retaining saddle 187 on the proximal end 180 of the driver 116. The driver 116 extends from a proximal end 180 to a distal end 182 along the central longitudinal axis L. The driver shaft 188 is configured to be received through the channel 165 of the threaded shaft 112. The distal end 182 of the driver 116 includes a driving tip configured to engage the recess 61 in the screw head 62 of the implant 10.

Figure 42:
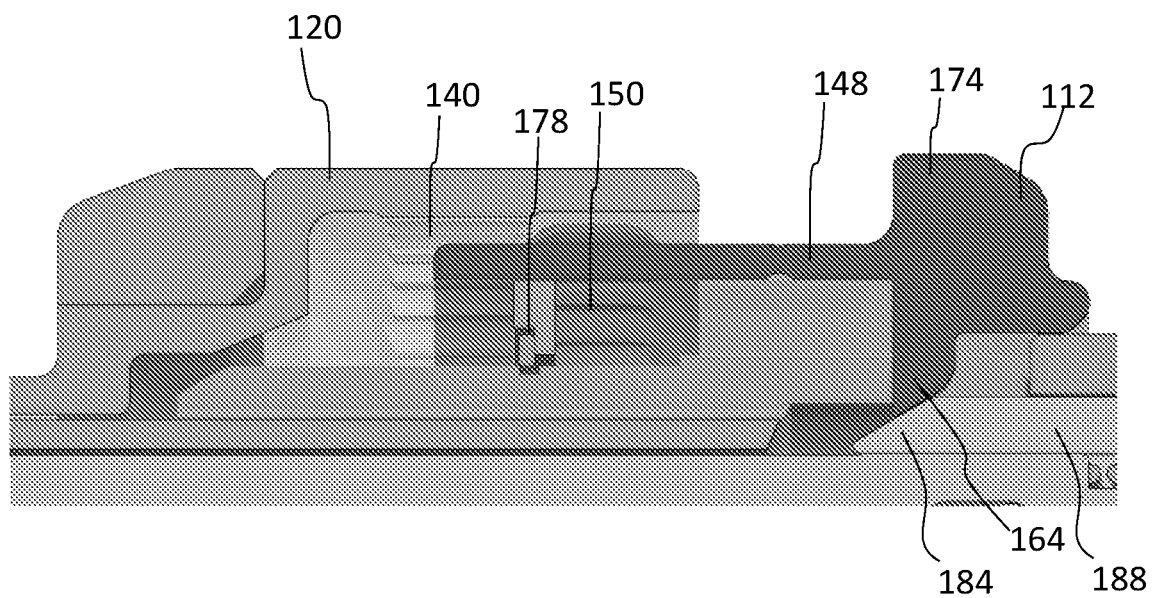
FIG. 42 is a partial cross-sectional view with the driver engaging and the splines disengaged.
Figure 43:
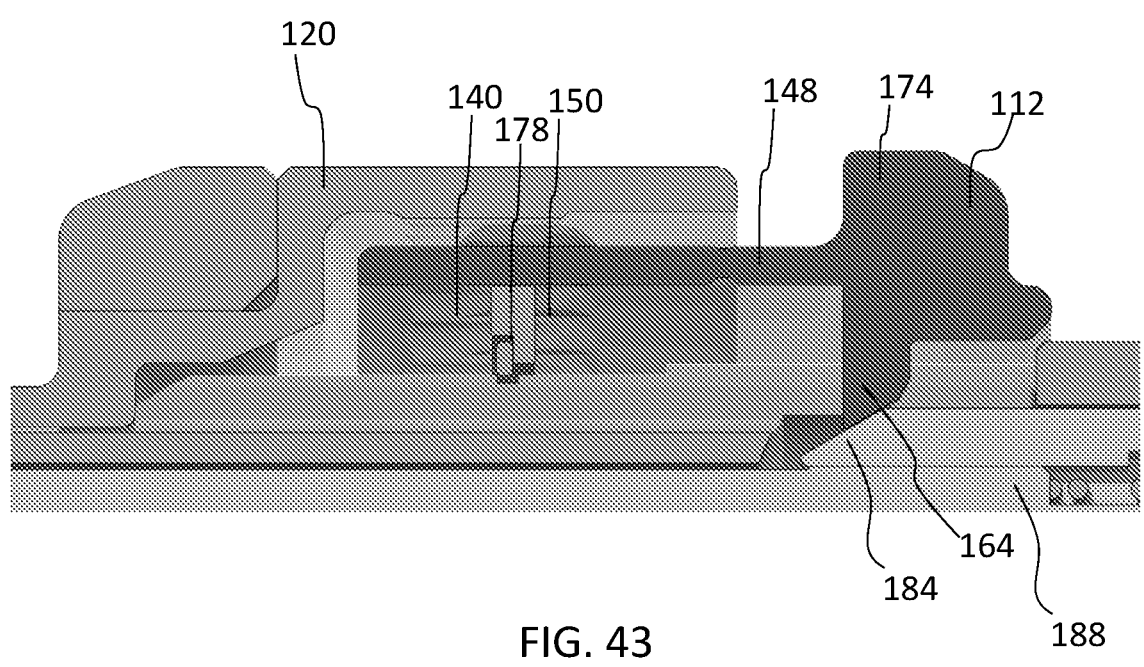
FIG. 43 is a partial cross-sectional view with the driver fully engaged and the splines engaged.

As best seen in FIGS. 42-44, the driver shaft 188 includes a linear cam 184 configured to engage the slider 148 of the threaded shaft 112. The linear cam 184 may be engaged with an engagement member 164 of the threaded shaft 112, thereby linearly translating the slider 148 to engage the splines 140, 150 as described in more detail herein. The linear cam 184 may include one or more protruding cam surfaces, such as angled surfaces configured to mate with corresponding surfaces on the engagement member 164 of the slider 148. As the driver 116 is placed through the channel 165 of the threaded shaft 112, the linear cam 184 of the driver 116 may push on engagement members 164 of the slider 148, thereby linearly translating the slider 148 forward and causing the splines 140, 150 to mate.

The driver shaft 188 may also define an annular groove 185 around the perimeter of the shaft 188 configured to receive the button 170 of the threaded shaft 112. In order to remove the driver 116 from the assembly, the button 170 must be depressed. Then, as the driver 116 is withdrawn the spline slider 148 slides linearly away from the distal end 132 of the guide shaft 120, thereby causing the splines 140, 150 to separate and become disengaged.

Figure 46:
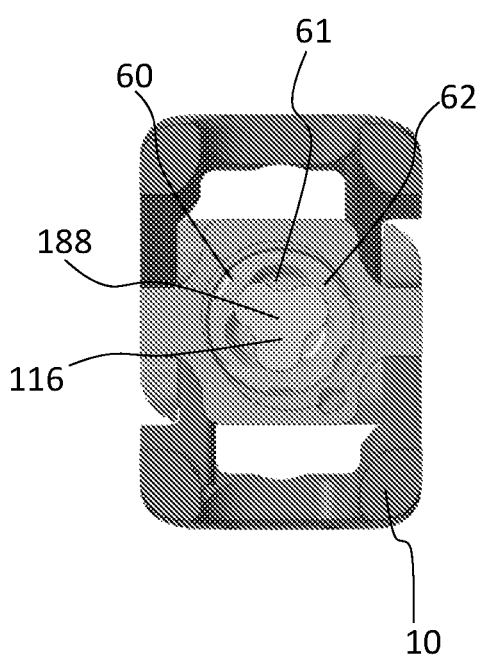
FIG. 46 is a view of the drive screw mechanism with the driver mismatched.
Figure 47:
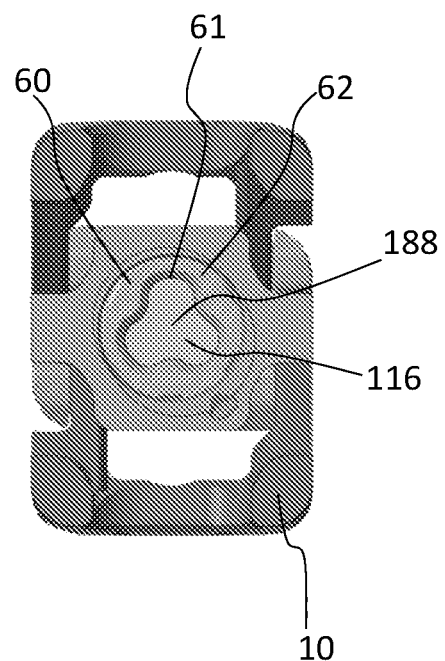
FIG. 47 is a view of the drive screw mechanism with the driver properly seated.

As best seen in FIGS. 46 and 47, the driver 116 allows for engagement into the drive screw 60 regardless of orientation. FIG. 46 depicts the driver 116 mismatched with the opening 61 of the drive screw 60. In particular, the tri-wing tip at the distal end 182 of the driver shaft 188 of the driver 116 is offset relative to the tri-wing recess 61 in the screw head 62 of the implant 10. Thus, the driver 116 is not properly seated in the drive screw 60. FIG. 47 depicts the driver 116 properly seated in the drive screw 60 of the implant 10. The tri-wing tip of the driver 116 is aligned with the tri-wing recess 61 of the screw head 62 of the implant 10. Thus, the driver 116 is properly seated in the drive screw 60. The engagement spring 190 in the proximal end 180 of the driver 116 allows for engagement into the drive screw 60 regardless of orientation. If the driver 116 is mismatched to the drive screw 60 as the splines 140, 150 in the back of the inserter 110 engage, the engagement spring 190 allows for the driver 116 to push backwards so that the splines 140, 150 can still engage. Once the driver 116 is rotated, the spring force from the engagement spring 190 will force the driver 116 to seat within the drive screw 60.

The overall length of the driver 116 may vary in accordance with the size of the implant 10 that is to be implanted. As the driver 116 is pushed through the threaded shaft 112, eventually the distal tip 182 will come into contact with the drive screw 60 within the implant 10. The location of the drive screw 60 varies relative to the back of the implant 10 with respect to length of the implant 10. The longer the implant 10, the longer the distance from the back of the implant 10 to the drive screw 60. Different length drivers 116 allow for the use of the same inserter 110, while still accommodating different length implants 10.

Figure 48:
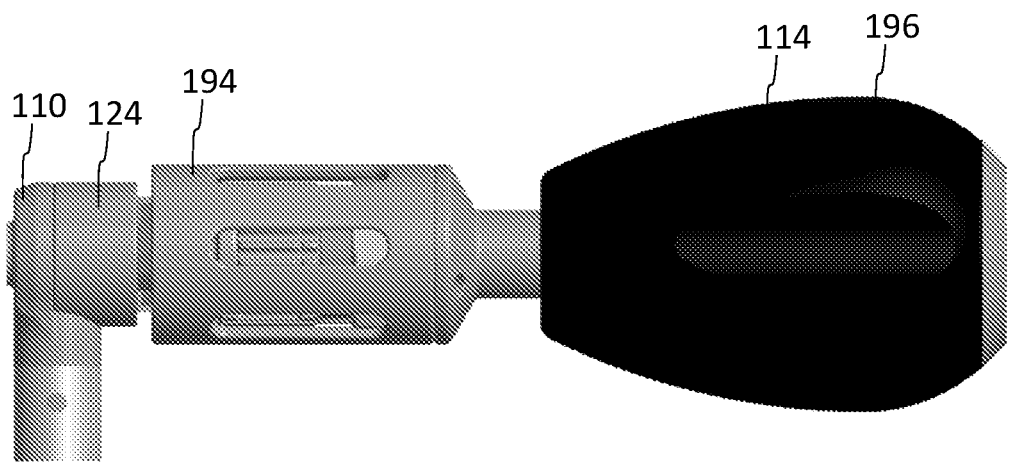
FIG. 48 is a close-up side view of a torque limiting handle attached to the inserter.
Figure 49:
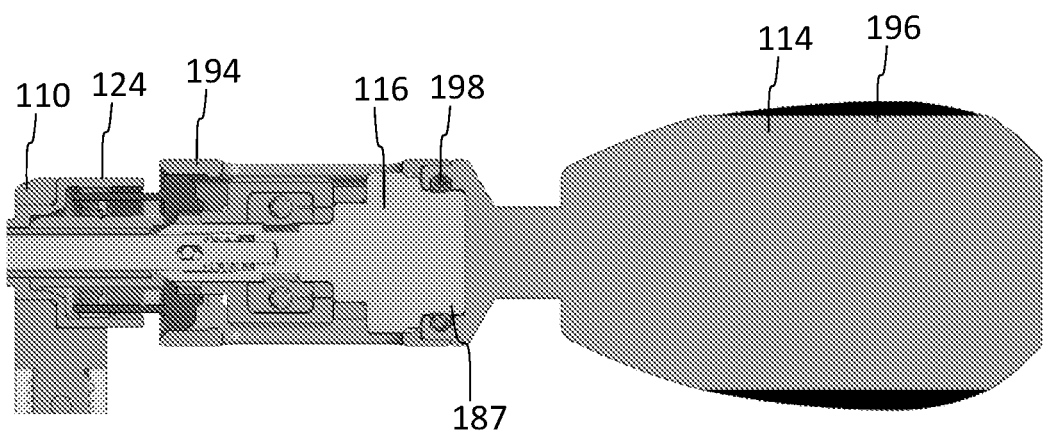
FIG. 49 is a cross-sectional view of the torque limiting handle of FIG. 48.

With emphasis on FIGS. 48 and 49, the drive handle 114 is shown. The drive handle 114 may have an attachment member 194 configured to mate with the handle retaining saddle 187 of the driver 116 and a grip member 196 configured to be rotated manually by hand. The drive handle 114 may be configured as a torque limiting handle 114. The handle retaining saddle 187 on the proximal end 180 of the driver 116 allows for the torque limiting handle 114 to securely attach to the inserter instrument 100. The torque limiting handle 114 may have a cylindrical canted spring 198 embedded inside the attachment member 194. When the handle 114 is attached to the driver 116, the cylindrical canted spring 198 seats within the handle retaining saddle 194 such that when the inserter instrument 100 is inverted, the torque limiting handle 114 will not fall off.

Instruments may be dropped in the operating room. If components are not secured directly to each other, they may easily disassemble. Engagement features like the spring tab 122, the driver engagement button 170, and/or the cylindrical canted spring 198 inside the torque limiting handle 114 may help to ensure that the instruments stay affixed to each other while the implant 10 is being inserted.

Figure 50:
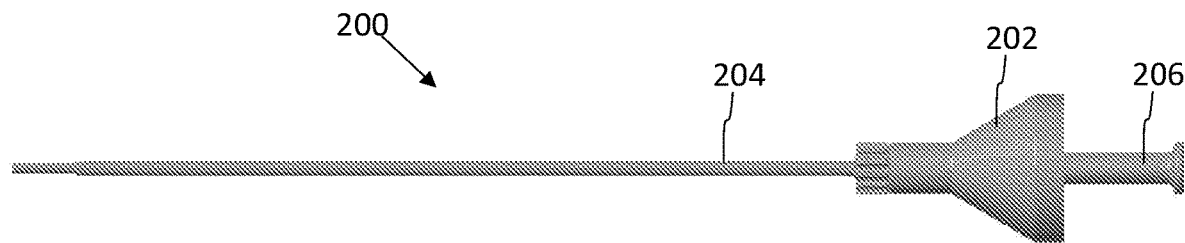
FIG. 50 is a side view of a bone funnel according to one embodiment.
Figure 51:
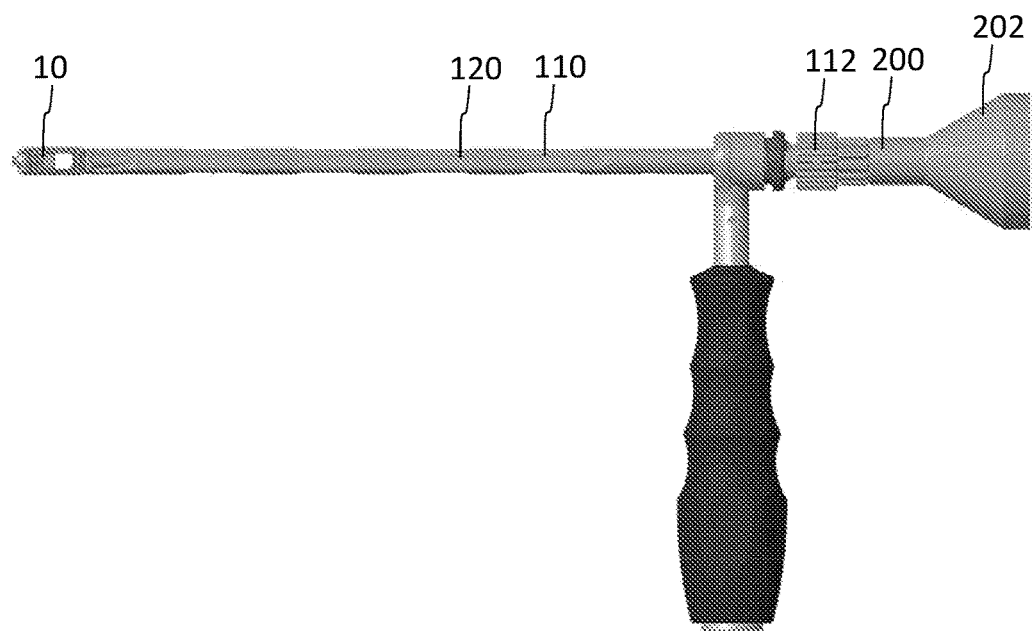
FIG. 51 shows an assembled view of the bone funnel of FIG. 50 and the inserter of FIG. 31.

Turning now to FIGS. 50 and 51, a bone funnel assembly 200 is shown. The bone funnel assembly 200 is configured to be used with the inserter sleeve 110 and the threaded shaft 112 of the inserter instrument 100. The threaded shaft 112 is cannulated through the length of the instrument. When the inserter sleeve 110 is attached to the implant 10, and no driver 116 is connected, the cannulation is one continuous diameter through to the back of the implant 10. This allows for the bone funnel assembly 200 to be placed down through the inserter instrument 100 and align with the cannulation in the back of the implant 10. Bone graft can then be placed through the funnel tube 204 to fill the inside of the implant 10, while the implant 10 is within the disc space.

The bone funnel assembly 200 includes a bone funnel 202 and a funnel tube 204. The bone funnel 202 may thread onto the funnel tube 204 or be otherwise suitably affixed. The bone funnel assembly 200 is configured to slide through the threaded shaft 112 and/or the guide shaft 120. The bone funnel tube 204 is free to axially translate up and down the threaded shaft 112 and/or the guide shaft 120. A graft pusher 206 is a cylindrical shaft that slides down the funnel tube 204 and pushes the graft material out the other end into the implant 10.

The geometric shape of the funnel 202 allows for ease of placement of material and the graft pusher 206 ensures ease of installation of material down the inserter 100. Thus, the insertion system provides for ease of backfill to the implant 10 as well as ease of installation of material down the inserter 100.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. An implantable system comprising:
an expandable device comprising a first endplate, a second endplate, a body positioned between the first endplate and the second endplate;
a drive screw and a lock positioned within the body, wherein rotation of the drive screw is configured to increase or decrease a distance between the first endplate and the second endplate, and the lock is configured to stop rotation to the drive screw,
the drive screw having a head portion and a shaft,
the lock having a first ring and a second ring,
wherein in a locked position, the second ring rests in a circumferential groove of the head portion and the first ring of the lock rests on a top face of the head portion,
wherein in an unlocked position, the second ring is translated out of the groove thereby permitting the drive screw to rotate by a driver.

2. The implantable system of claim 1, wherein the first ring of the lock is a full ring and includes a strut attached to the second ring and configured to be received in any one of a plurality of notches in the locked position, the strut having a radially outward projection received in a recess of the body, the recess having a sufficient depth to retain the strut when the strut of the first ring translates out of the notch to place the lock in the unlocked position.

3. The implantable system of claim 1, wherein the first ring includes an off center through hole.

4. The implantable system of claim 1, wherein the second ring of the lock is a C-shaped spring ring.

5. The implantable system of claim 1, wherein a plurality of protrusions and a plurality of notches are located radially around a tip of the head portion, wherein in the locked position, the first ring rests in any one of the notches.

6. The implantable system of claim 5, wherein the plurality of protrusions include quadrilateral projections.

7. The implantable system of claim 1, wherein the expandable device further includes a retaining ring configured to retain the lock and drive screw in the body of the expandable device.

8. The implantable system of claim 7, wherein the retaining ring has a generally C-shaped body.

9. The implantable system of claim 8, wherein the retaining ring includes a plurality of outer radial notches and a plurality of inner radial notches that allow the retaining ring to deflect without deforming.

10. The implantable system of claim 1, wherein the expandable device further includes a friction ring configured to reduce an expansion force and add friction to the drive screw.

11. The implantable system of claim 10, wherein the friction ring is an annular ring having an outer surface configured to contact the body and an inner surface configured to contact the shaft of the drive screw.

12. An implantable system comprising:
an expandable device comprising a first endplate, a second endplate, a body positioned between the first endplate and the second endplate;
a drive screw and a lock positioned within the body, wherein rotation of the drive screw is
configured to increase or decrease a distance between the first endplate and the second endplate, and the lock is configured to stop rotation to the drive screw,
the drive screw having a head portion and a shaft,
the lock having a ring,
wherein in a locked position, the ring rests in a groove of the head portion,
wherein in an unlocked position, the ring is translated out of the groove thereby permitting the drive screw to rotate by a driver.

13. The implantable system of claim 12, wherein the ring of the lock is a C-shaped spring ring.

14. The implantable system of claim 12, wherein a plurality of protrusions and a plurality of notches are located radially around a tip of the head portion.

15. The implantable system of claim 14, wherein the plurality of protrusions include quadrilateral projections.

16. The implantable system of claim 12, wherein the expandable device further includes a retaining ring configured to retain the lock and drive screw in the body of the expandable device.

17. The implantable system of claim 16, wherein the retaining ring has a generally C-shaped body.

18. The implantable system of claim 17, wherein the retaining ring includes a plurality of outer radial notches and a plurality of inner radial notches that allow the retaining ring to deflect without deforming.

* * * * *